US006673598B1

(12) United States Patent
Akers et al.

(10) Patent No.: US 6,673,598 B1
(45) Date of Patent: Jan. 6, 2004

(54) DISPOSABLE CULTURE BAG

(75) Inventors: Roger Akers, Houston, TX (US); William J. Anderson, Richmond, TX (US); Stephen S. Navran, Jr., Houston, TX (US); Adrian F. Dinges, Jr., Houston, TX (US)

(73) Assignee: Synthecon, Inc., Houston, TX (US)

(*) Notice: Subject to any disclaimer, the term of this patent is extended or adjusted under 35 U.S.C. 154(b) by 0 days.

(21) Appl. No.: 10/283,000

(22) Filed: Oct. 29, 2002

(51) Int. Cl.[7] ................................................ C12M 1/10

(52) U.S. Cl. ............................... 435/298.2; 435/297.2; 435/297.3; 435/297.5

(58) Field of Search .......................... 435/289.1, 297.1, 435/297.2, 297.3, 298.2, 297.5; 383/33, 36, 66, 67, 78, 88, 100, 109, 116

(56) References Cited

U.S. PATENT DOCUMENTS 3,946,780 A 3/1976 Sellers
4,027,427 A 6/1977 Stoller et al. ................ 47/1.1
4,391,912 A 7/1983 Yoshida et al.
4,908,315 A 3/1990 Kertz
4,939,151 A 7/1990 Bacehowski et al.
5,057,429 A 10/1991 Watanabe et al.
5,071,760 A 12/1991 Watanabe et al.
5,225,346 A 7/1993 Matsumiya et al.
5,523,228 A 6/1996 Ingram et al.
6,022,733 A * 2/2000 Tam et al. .............. 435/287.1
6,068,970 A 5/2000 Hosono et al.
6,245,555 B1 6/2001 Curtis
6,379,949 B1 4/2002 Ward

* cited by examiner

*Primary Examiner*—David A. Redding
(74) *Attorney, Agent, or Firm*—Elizabeth R. Hall

(57) ABSTRACT

A cell culture bag for culturing cells, cellular aggregates, particles, tissues and organoids is disclosed. The cell culture bag is a flexible and disposable culture bag that fits within a bag support chamber of a bioreactor. The cell culture bag has an inlet means and an outlet means for the introduction and removal of media. Certain embodiments of the culture bag have an inlet and outlet fluid coupling swivel joint and/or perforated perfusion tubes extending from the inlet means into the interior of the bag to assist in mass transfer and mixing the media to maintain an even temperature throughout the culture bag.

51 Claims, 13 Drawing Sheets

13
31
29
25
2
21
11
28a
26
28a
27
24
22a
14
22a
23
23
40
12
44
41
65
66
69
68
63
68
66
65
62
60
61

3
4
6
13
14
20
21
22a
22a
23
23
24
25
26
27
28a
28a
29
30
31
34
35
36
37
40
41
42
43
44
48
49
51
52
60
61
62
63
65
65
66
66
68
68
69

300
348
349
339
340
346
341
326
343
328
342
322
327
323
324
21
318
329
332
383
333
330
331
381
382
380

384
356
358
21
360
355
354
364
366
359
367
357
363
370
365
368
369

11
12
13
14
21
25
29
30
31
34
35
36
37
40
41
42
43
44
48
49
51
52
60
61
62
63
65
66
68
69
500

DISPOSABLE CULTURE BAG

BACKGROUND OF THE INVENTION

1. Field of the Invention

The present invention relates to a disposable culture bag for culturing cells, cellular aggregates, particles, tissues and organoids. More particularly, the present invention relates to a flexible, disposable culture bag having an inlet and outlet for the introduction and removal of media under sterile conditions.

2. Description of the Related Art

The expense of producing biologicals in aseptic bioreactors is exacerbated by the required cleaning, sterilization and validation of the standard stainless steel or glass bioreactors by the customer. Attempts have been made to solve this problem with the development of presterilized disposables that need not be cleaned, sterilized or validated by end users. The use of such disposables would provide savings of thousands of dollars and multiple hours of labor per run. Furthermore, plastics are lightweight, easy to transport, and require less room than stainless steel or glass vessels.

For example, U.S. Pat. No. 6,245,555 B1 describes a bioreactor having a support housing. The interior chamber of the support housing is lined with a disposable liner and sealed with a head plate attached to the liner to form a sealed chamber. Since the liner is open at the top, it must be used in a vertically oriented bioreactor to prevent the contamination of the head plate. Although this system provides a disposable liner, the head plate and the interior chamber will still require cleaning and sterilization. In addition, oxygen transfer is limited by the air-liquid surface. As the vessel becomes larger, the air-liquid interface becomes smaller relative to the process volume.

Another solution has been to develop flexible, disposable plastic vessels that do not require cleaning or sterilization and require only minimal validation efforts. For example, U.S. Pat. No. 5,523,228 describes a flexible, disposable, and gas permeable cell culture chamber that is horizontally rotated. The cell culture chamber is made of two sheets of plastic fused together. The edges of the chamber, beyond the seams, serve as points of attachment to a horizontally rotating drive means. The cell culture chamber is made of gas permeable material and is mounted on a horizontally rotating disk drive that will support the flexible cell culture chamber without blocking airflow over the membrane surfaces. Thus, the cell culture chamber is placed in an incubator and oxygen transfer controlled by controlling the gas pressure in the incubator according to the permeability coefficient of the bag. The rotation of the bag assists in mixing the contents of the bag and enhances gas transfer throughout the bag. However, the cell culture chamber is limited to use within a controlled gas environment. Furthermore, the cell culture chamber has no support apparatus and is therefore limited to small volumes. The described cell culture chamber is actually a batch culture device in that it does not provide an inlet and an outlet for media to be constantly pumped into and out of the chamber during rotation.

Wave Biotech (Bridgewater, N.J.) has also developed a range of presterile, disposable bioreactors that do not require cleaning or sterilizing. The Wave Bioreactor® is made of sheets of flexible, gas impermeable material. The bag is partially filled with media and then inflated with air that continually passes through the bag's headspace. The media is mixed and aerated by rocking the bags up to 40 times a minute to increase the air-liquid interface. However, since a solid housing does not support the bags, the bags become unwieldy and difficult to handle as they increase in size. Furthermore, the wave action within the rocking bag creates damaging turbulent forces. Certain cell cultures, particularly human cell cultures, thrive better under more gentle conditions.

There is a continuing need to develop lightweight, presterilized, disposable bioreactors with simple connections to existing equipment that require little training to operate, yet provide the necessary gas transfer and nutrient mixing required for successful cell cultures.

SUMMARY OF THE INVENTION

The invention contemplates a cell culture bag for culturing cells, cellular aggregates, particles, tissues and organoids. The cell culture bag is a flexible and disposable culture bag that fits within a support chamber of a bioreactor. The cell culture bag has an inlet means and an outlet means for the introduction and removal of media.

One aspect of the present invention is a culture bag having: (a) at least one sheet having a first end, a second end, an internal side, and an external side, where the internal side of the sheet is positioned to face an interior of the culture bag; (b) a seam formed by fusing overlapped sections of one or more sheets; (c) an inlet means fused to the first end of one or more sheet; (d) an outlet means fused to the second end of one or more sheet; and (e) at least one outer perfusion tube, wherein a proximal end of the outer perfusion tube is in fluid communication with the inlet means, a central section of an external surface of the outer perfusion tube is fused to an interior surface of the seam, and a distal end of the outer perfusion tube is closed.

Another aspect of the present invention is a culture bag having: (a) a bag of flexible material having a first end, a second end, an internal side, an external side and two opposed edges, wherein one edge of each sheet is fused with one edge of an adjacent sheet to form a seam, and wherein the internal sides of said fused sheets are positioned within an interior of the bag; (b) an inlet means fused to the first end of at least one sheet, wherein the inlet means includes an inlet end piece and an inlet fluid coupling swivel joint; and (c) an outlet means fused to the second end of at least one sheet, wherein the outlet means comprises an outlet end piece and an outlet fluid coupling swivel joint.

Yet another aspect of the present invention is a culture bag having: A culture bag comprising: (a) at least one sheet having a first end, a second end, an internal side, and an external side, wherein the internal side of said sheet is positioned to face an interior of the culture bag; (b) a seam formed by fusing overlapped sections of one or more sheets; (c) an inlet means fused to the first end of one or more sheet; (d) an outlet means fused to the second end of one or more sheet; (e) at least one outer perfusion tube, wherein a proximal end of the outer perfusion tube is in fluid communication with the inlet means, a central section of an external surface of the outer perfusion tube is fused to an interior surface of the seam, and a closed distal end, said central section of the outer perfusion tube being perforated to allow fluid communication between the lumen of the outer perfusion tube and the interior of the culture bag; and (f) at least one internal perfusion tube, wherein a proximal end of the internal perfusion tube is in fluid communication with the inlet means, a perforated central section allow fluid communication between the lumen of the internal perfusion tube and the interior of the culture bag, and a closed distal end.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

The culture bag of the present invention provides a flexible, disposable culture bag for culturing cells, cell aggregates, particles, tissues and organoids. The disposable culture bag is designed to fit into a horizontally rotating support device or chamber of a bioreactor. The disposable bag allows a user to quickly change from one cell line or tissue to another with the insertion of a new culture bag into the bioreactor chamber. The culture bag optionally includes an inlet and outlet fluid coupling swivel joint and/or perfusion tubes. The perfusion tubes allow fluid entering through the inlet means of the culture bag to perfuse throughout the interior of the bag and assist in mixing the media within the culture bag.

Figure 1:
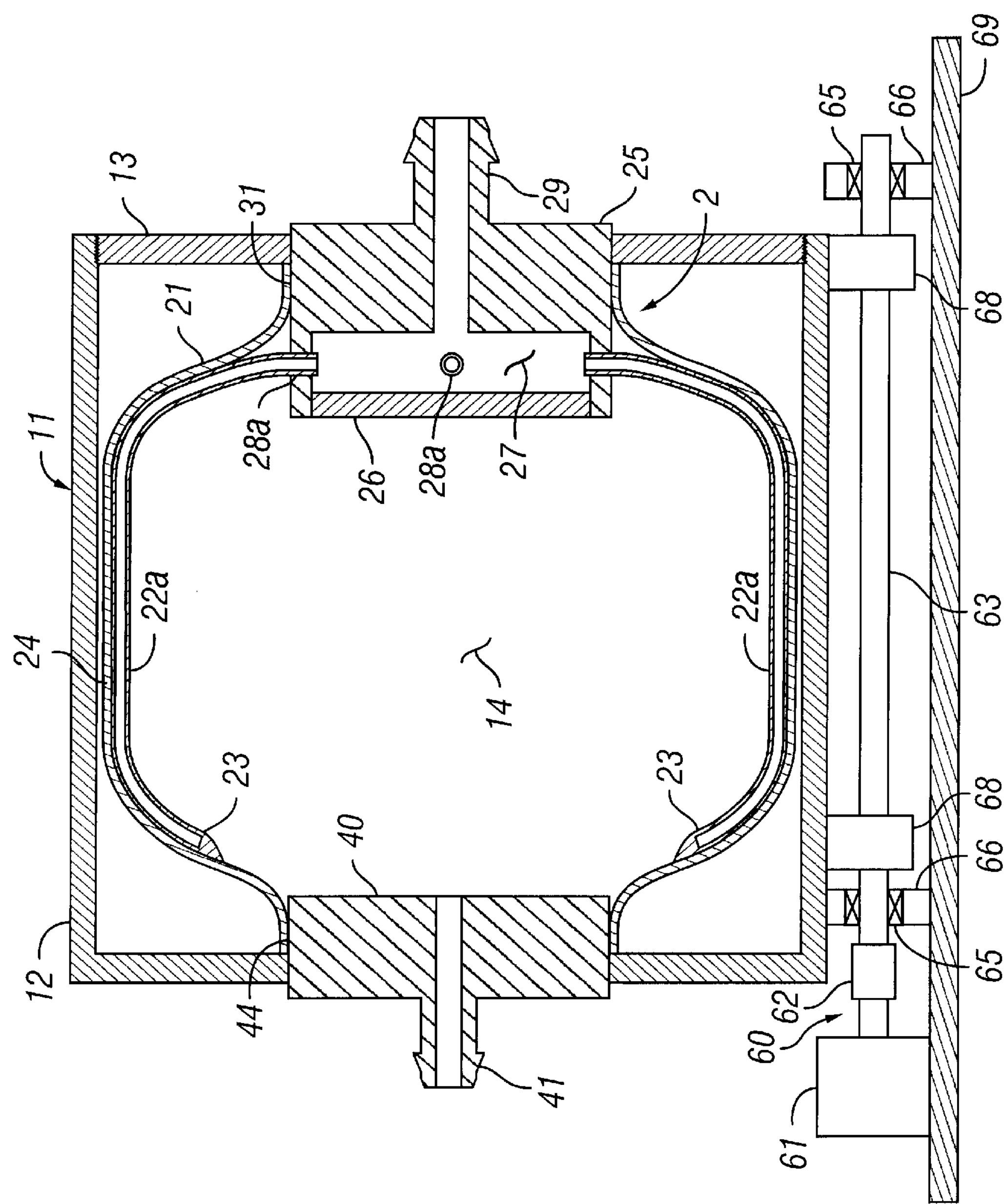
FIG. 1 shows a partial longitudinal cross-section of one embodiment of the culture bag, as well as a bag support assembly or chamber and a mechanism for rotating the bag support assembly and culture bag.

Referring now to the drawings, and initially to FIG. 1, it is pointed out that like reference characters designate like or similar parts throughout the drawings. The Figures, or drawings, are not intended to be to scale. For example, purely for the sake of greater clarity in the drawings, wall thickness and spacing are not dimensioned as they actually exist in the assembled embodiment.

FIG. 1 shows a partial longitudinal section of one embodiment of a culture bag of the present invention installed in a rotating chamber, or bag support device or assembly. The primary elements shown are a rotatable bag support assembly 11, a bag assembly 2 housed within and supported by the bag support assembly 11, and a drive assembly 60 that rotates the bag support assembly and its enclosed bag assembly 2. Preferably, the bag support assembly and its enclosed bag assembly will be rotated about the longitudinal axis of the bag support assembly. However, the bag support assembly and the enclosed bag assembly may be tilted and rotated at an angle from the longitudinal axis of the bag support assembly.

Figure 2:
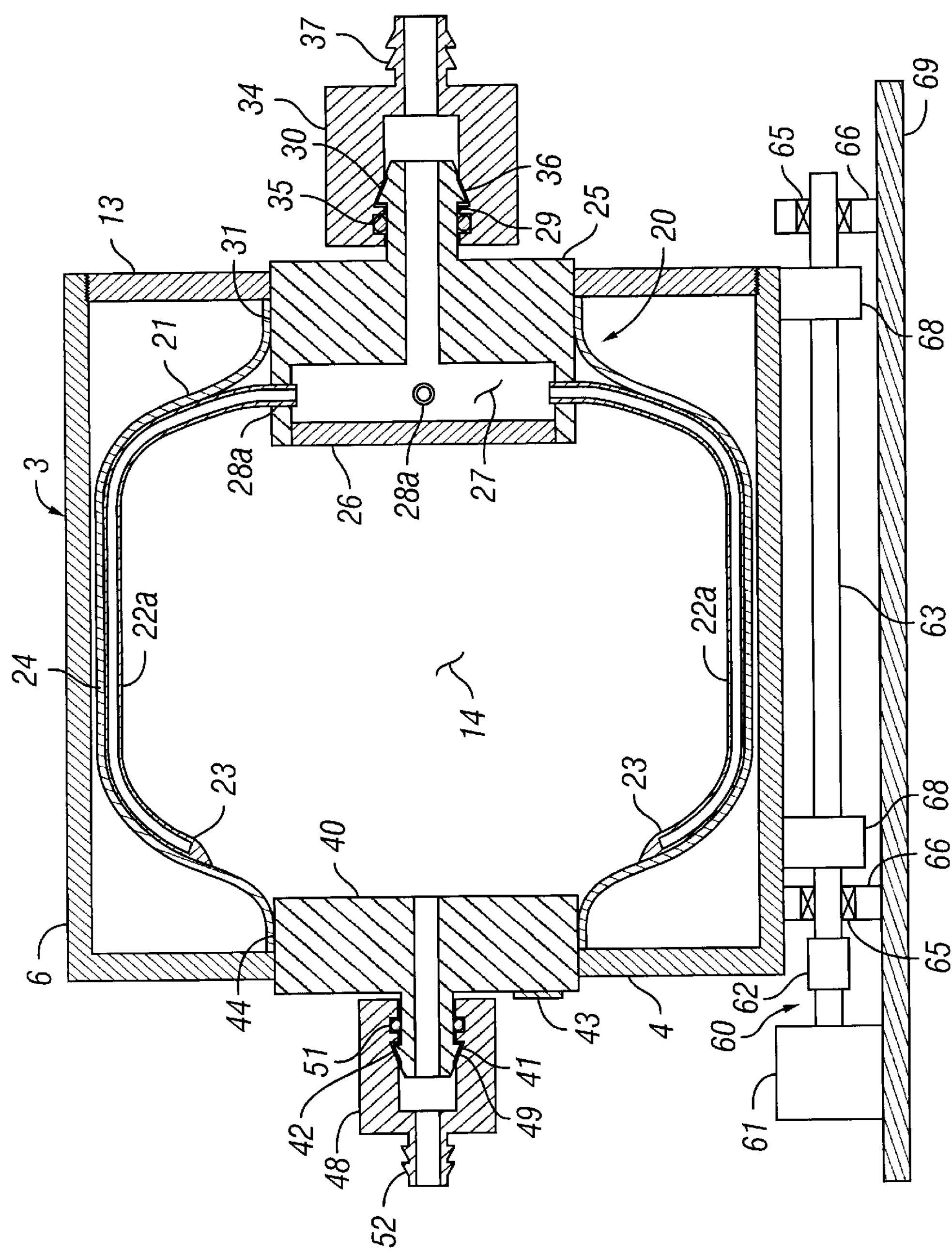
FIG. 2 shows a partial longitudinal cross-section of another embodiment of the culture bag that includes an inlet and an outlet fluid coupling swivel joint, as well as the bag support assembly and mechanism for rotating the bag support assembly and culture bag.
Figure 22:
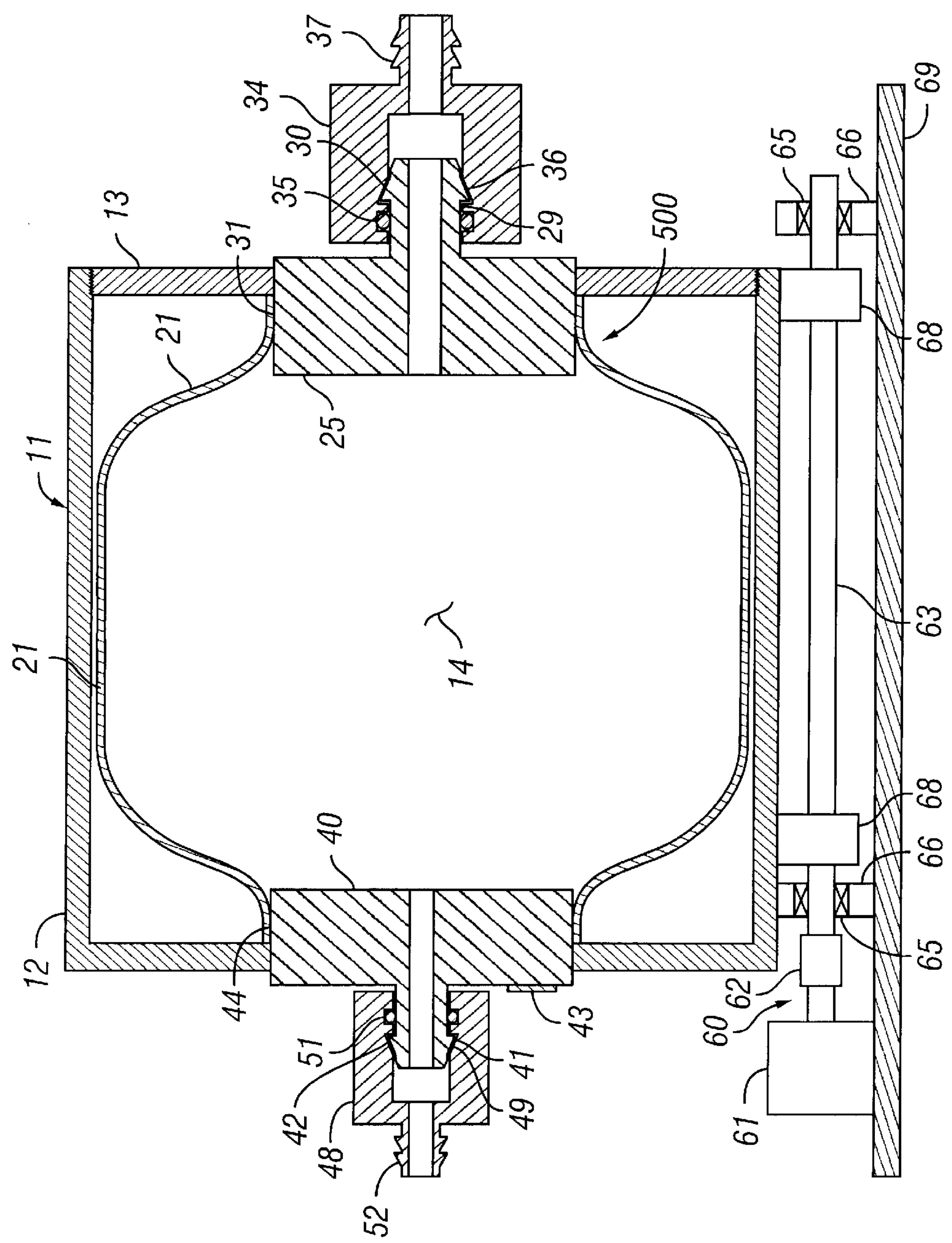
FIG. 22 shows a partial longitudinal cross-section of an embodiment of the culture bag that includes an inlet and an outlet fluid coupling swivel joint, as well as the bag support assembly and mechanism for rotating the bag support assembly and culture bag.

FIG. 2 shows a partial longitudinal section of an alternative embodiment of the culture bag installed in the rotating chamber, or bag support assembly 11. The bag assembly 20 is very similar to the bag assembly 2 shown in FIG. 1; except that bag assembly 20 includes an inlet fluid coupling swivel joint 34 and an outlet fluid coupling swivel joint 48. FIG. 22 shows yet another embodiment of the bag assembly 500, that is similar to the bag assembly 20, except that the bag assembly 500 does not have perfusion tubes extending from the inlet means of bag assembly 500 into the interior of the culture bag.

Figure 3:
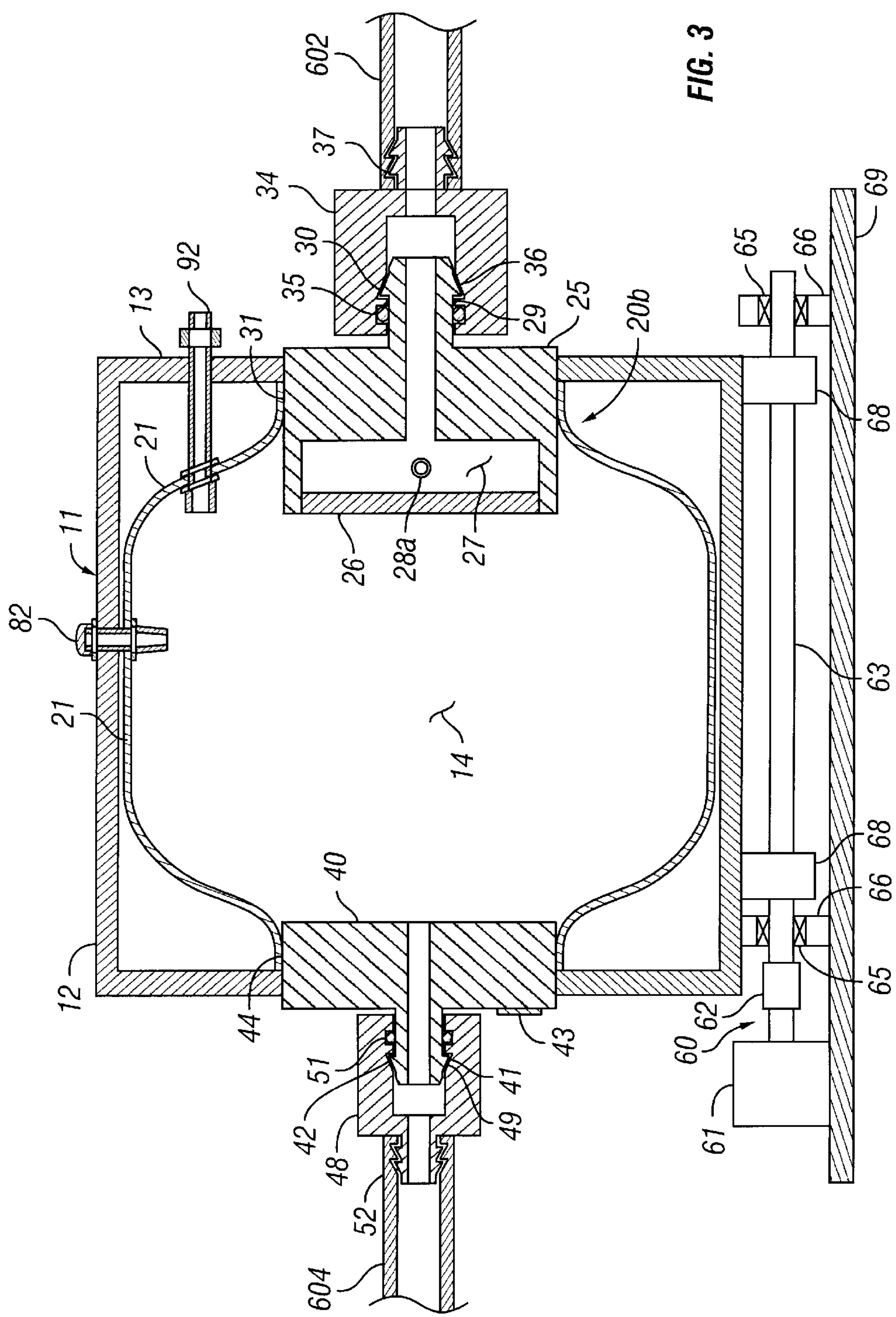
FIG. 3 shows a partial longitudinal cross-section of the culture bag taken between the seams of the culture bag.

FIG. 3 shows a partial longitudinal section of an embodiment of the culture bag assembly 20 taken between the seams of the culture bag 21 in order to show a gas removal port 82 and a fill port 92. Furthermore, FIG. 3 shows the culture bag assembly 20 with an attached inlet system tubing assembly 602 and an outlet system tubing assembly 604. The culture bag 2, 20 or 500 may also have a complete loop connected to a media bag on one end, to a waste bag on the other end, and to an optional media recycling loop.

Numerous configurations of a bag support assembly can be used. One example of a bag support assembly 11, shown in FIGS. 1 and 2, consists of bag support end 12 and bag support closure 13. The bag support assembly 11 may be constructed of a variety of materials known in the art, but will preferably be constructed of either a metal, such as stainless steel, or a solid plastic, such as Plexiglas or acrylic. Although the bag support assembly may be made any shape, the bag support assembly is preferably cylindrical to ease its horizontal rotation.

Figure 4:
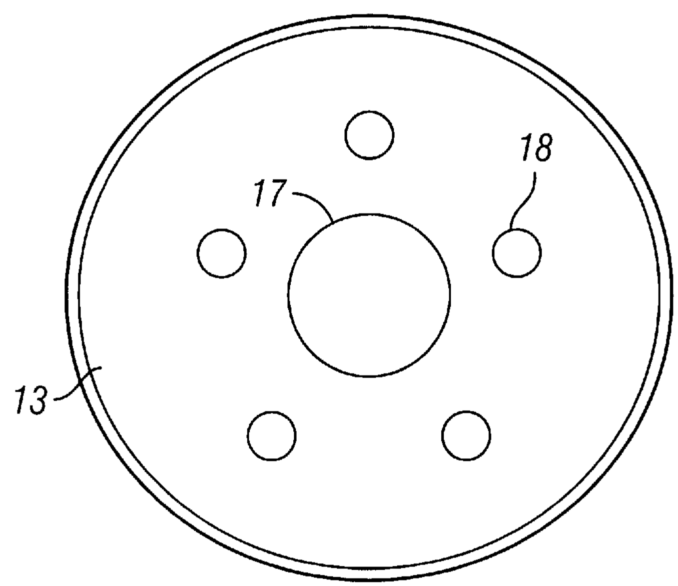
FIG. 4 shows an end view of an embodiment of a bag support assembly.

Bag support end 12 has a thin walled right circular cylindrical section and a transverse bulkhead at a first end of the cylindrical section. The transverse bulkhead has a thickness of approximately 0.5 to 0.1 inch and a concentric circular hole. The cylindrical section has female threads at its second, opposed end. Bag support closure 13 is a round disk with a central circular hole and a thickness of approximately 0.5 to 0.1 inch. The exterior cylindrical surface of bag support closure 13 has male threads comatable with the female threads of bag support end 12 so that the two items may be screwed together to create a housing having coaxial end holes. As illustrated in FIG. 4, the bag support closure 13 has a variety of bores. The central bore 17 is designed to fit the inlet piece 25 and outer bores 18 are designed to fit gas removal ports 82 or fill ports 92. All of the bores in the bag support closure 13 are smooth and suitable for providing a support surface for closely fitting mating cylinders, ports, and tubing positioned within.

Figure 5:
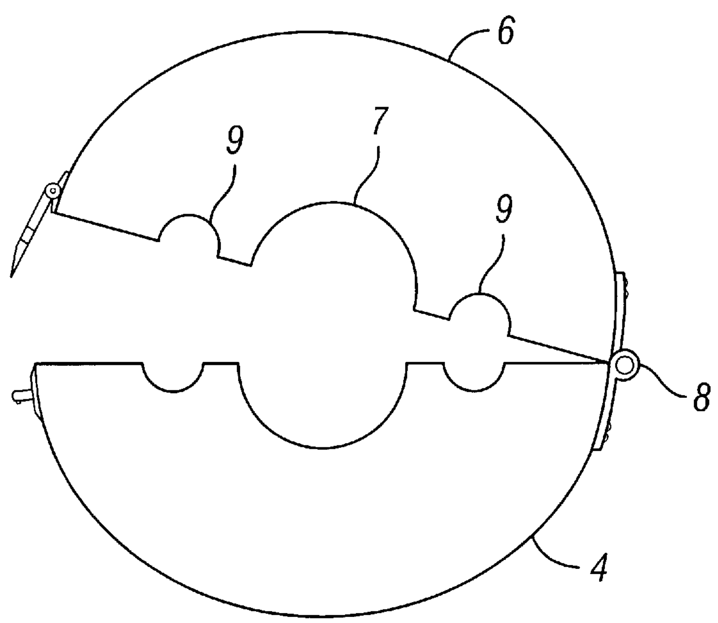
FIG. 5 shows an end view of an embodiment of a bag support assembly.
Figure 6:
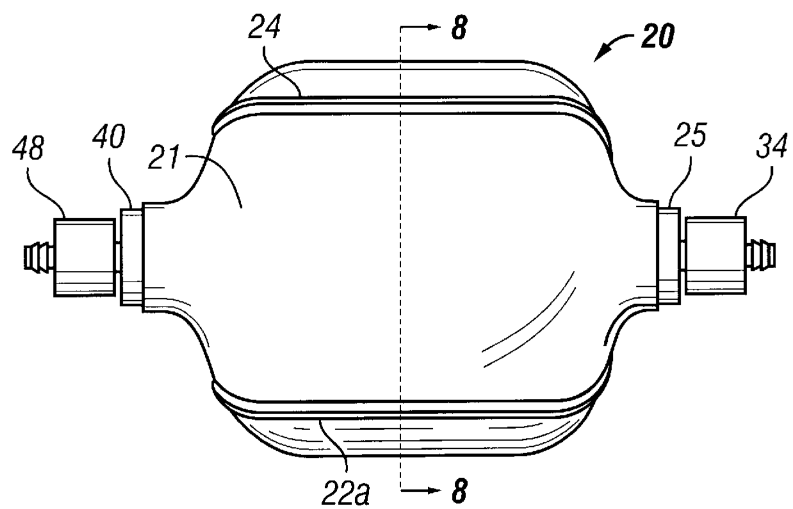
FIG. 6 shows a profile view of the culture bag shown in FIG. 2.
Figure 7:
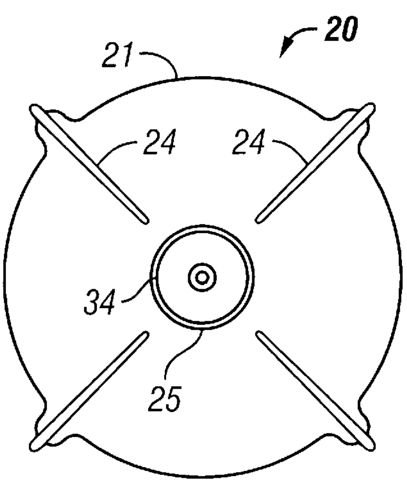
FIG. 7 shows an end view of the culture bag of FIG. 6 as seen from the inlet end.
Figure 8:
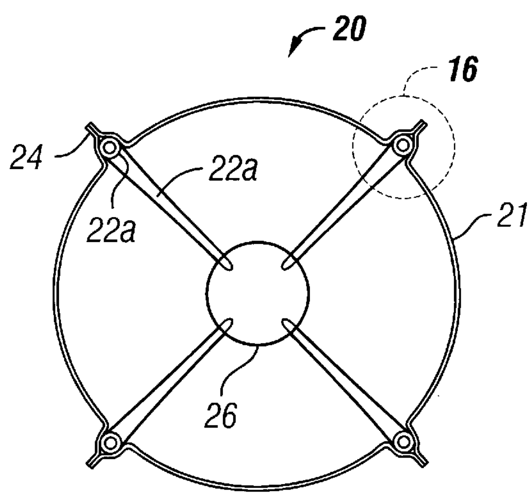
FIG. 8 is a transverse cross-section of the culture bag of FIG. 6 taken along line 8—8.
Figure 9:
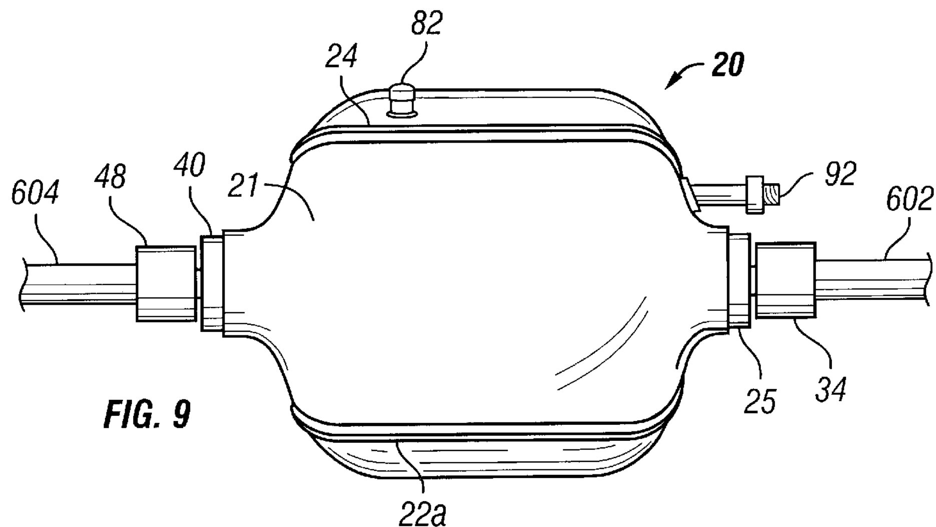
FIG. 9 shows a profile view of an embodiment of the culture bag of the present invention having a fill port, a gas removal port and an inlet and outlet system.

Another example of a bag support assembly is shown in FIG. 3. This bag support assembly 3 includes a top portion 6 and a bottom portion 4, where the top and bottom portions are hinged together. FIG. 5 shows an end view of this bag support assembly 3. Hinge 8 allows the top portion 6 and the bottom portion 4 of the bag support assembly 3 to open and close. A central concentric bore in the inlet end of the bag support assembly 3 is designed to fit around the inlet piece 25, while additional bores 9 are designed fit around gas removal ports 82 and fill ports 92. One advantage of bag support assembly 3 is that a bag assembly made with an inlet and outlet system incorporated into it, as shown in FIGS. 3 and 9, can be inserted into the bag support assembly 3 without having to disconnect any tubing or connectors.

As shown in FIGS. 1 and 2, bag assembly 2 and 20 include bag 21, outer perfusion tubes **22*a*, an inlet end piece 25 (for supplying perfusion tubes 22*a*), and an outlet end piece 40. Bag assembly 2 and 20 may also include one or more optional components such as internal perfusion tubes 22*b,c*, a gas removal port 82, and a fill port 92. Bag assemblies 2 and 20 have their constituent components welded or bonded or fused together. All of the components of bag assembly 2 and 20 which contact the biological media 14**, which are supplied to and removed from the bag assembly, are biologically non-reactive, non-toxic and exhibit low protein binding properties.

Bag assemblies 20 and 500, in contrast to the bag assembly 2, have an inlet fluid coupling swivel joint 34 and an outlet fluid coupling swivel joint 48 to allow the bag assembly 20 to freely rotate while connected to media input and output connectors. In contrast, bag assembly 2 would be hooked-up to media input and output systems that have swivel joints incorporated within the tubing connectors of the media input and output systems. The discussion of bag assembly 20 below will also apply to bag assembly 2, except for the inlet and outlet fluid coupling swivel joints of bag assembly 20.

Preferably the bag 21 is made of a plurality of layers such as the multilayered fabric construction used in the synthesis of custom bags manufactured by Newport Biosystems, Inc. (Anderson, Calif.). For example, a typical four-ply fabric construction would have individual layers, sequentially from the outer bag layer, of nylon, polyvinyldichloride (PVDC), a linear low density polyethylene (LLDPE), and a LLDPE inner layer for contacting the cells and the biological media. The plies of the bag have thicknesses with physical and molecular properties to provide the desired puncture strength, tensile strength, flexural strength, cell and gas and liquid permeabilities in appropriate ranges, and weldability and/or bondability or fusibility. The desired permeabilities typically are low or zero. However, variations of the bag 21 are designed to be gas-permeable for certain applications.

Since the bag assemblies 2, 20 and 500 are designed to be supported by a solid bag support system, large capacity bag assemblies can be used to scale-up production procedures. The bag assemblies 2, 20 or 500 are made to hold anywhere from milliliters of fluid to thousands of liters of fluid.

Normally joints between the segments of bag 21 or between bag 21 and the other components of the bag assembly 20 are made by fusing the two sides of the joint together with heat and pressure. Henceforth, the term fusing will be used with reference to joining elements of the bag systems of this invention, but it should be understood that adhesive or other bonding, ultrasonic welding, or other suitable means can be used to effect the connections.

The shape of the bag 21 is determined by the size and shape of the bag support assembly 11 to be used. Although a preferred embodiment of the bag 21 has an approximately cylindrical shape with rounded corners as illustrated in FIG. 2, the bag 21 can have other shapes. Bag 21 is typically designed to closely fit the size and shape of the interior of the bag support assembly 11 when the bag is filled.

Figure 16:
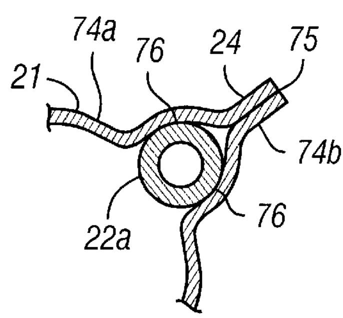
FIG. 16 is an enlargement of the cross-sectional area 16 of FIG. 8 showing a first arrangement of the perfusion tube-bag interface.

One possible means of construction of bag 21, shown in FIG. 16, uses precut gore segments **74*a,b* to produce the desired bag geometry wherein the openings in the bag ends are smaller than the bag outer diameter. The sides of gores 74*a,b* are fused to make a bag seam 24** by using a lap joint between the gores.

Figure 17:
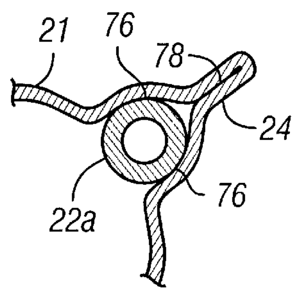
FIG. 17 shows an alternative arrangement of the perfusion tube-bag interface.
Figure 13:
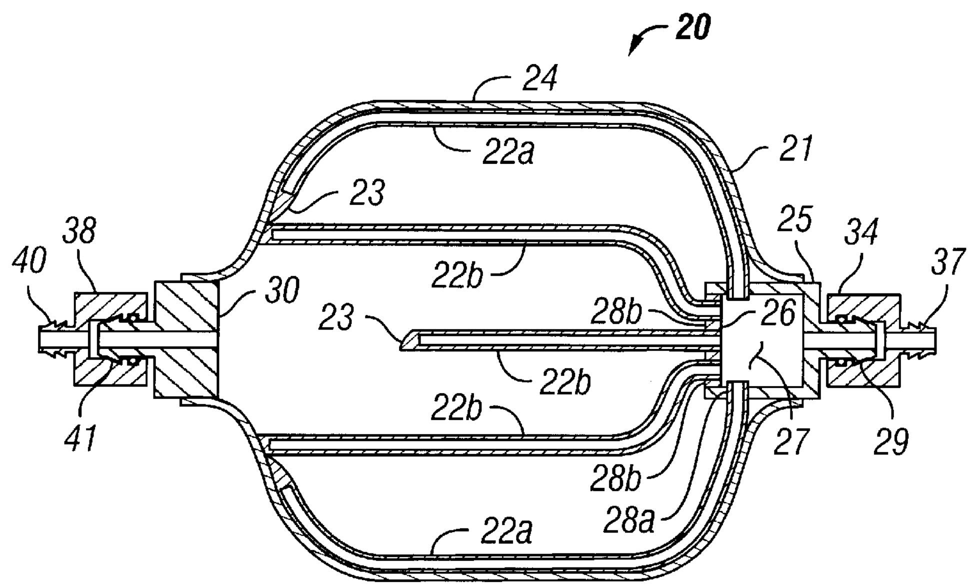
FIG. 13 is a longitudinal cross-section of another embodiment of the culture bag having the distal end of some of the internal perfusion tubes fused to the seam of the culture bag.
Figure 15:
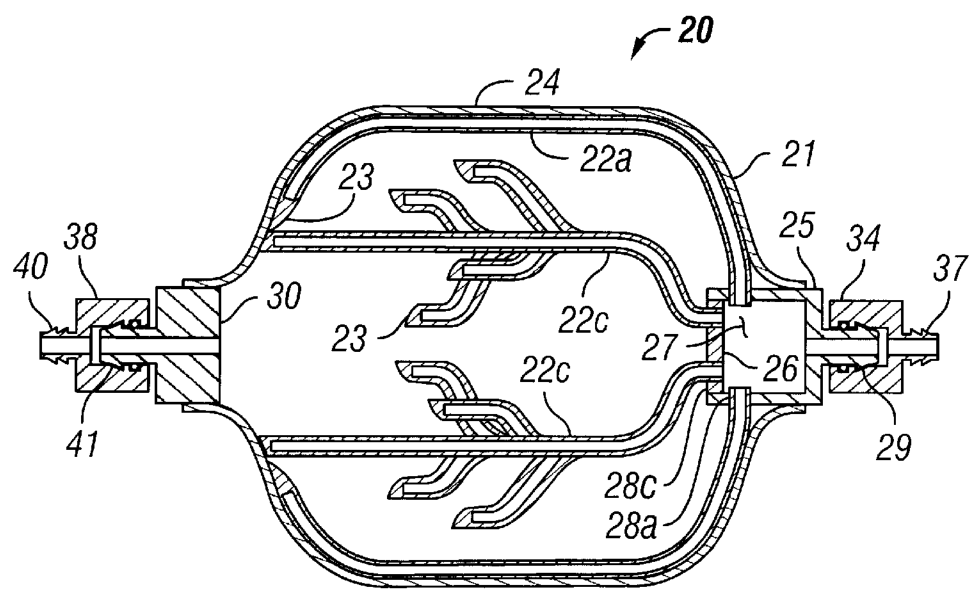
FIG. 15 is a longitudinal cross-section of an embodiment of the culture bag having branched internal perfusion tubes with some of the distal ends of the branched internal perfusion tubes fused to the seam of the culture bag.

FIG. 17 discloses a variant construction of seam 24, wherein the wall of bag 21 is lapped together by folding so that it may be fused in a lap joint 78. This approach permits using a one-piece tubular construction or a reduced number or gores for bag 21. The effective diameter of the bag at a given point in a seam 24 is determined by the amount of lap in the fold of seam 24 with this construction. If desired, the excess lap material of the alternate seam 24 shown in FIG. 17 may be trimmed off from the bag 21, or alternatively it may be folded to lie against the outer surface of the bag. Other types of joints may be used.

Alternatively, the exterior wall of the culture bags 2, 20, or 500 could be molded as a single piece rather than constructed from various sheets of material fused together. If the exterior wall of the culture bag were molded as a single piece, the outer perfusion tubes would be built into the molded wall of the culture bag rather than fused into a seam of the culture bag as described above.

Figure 10:
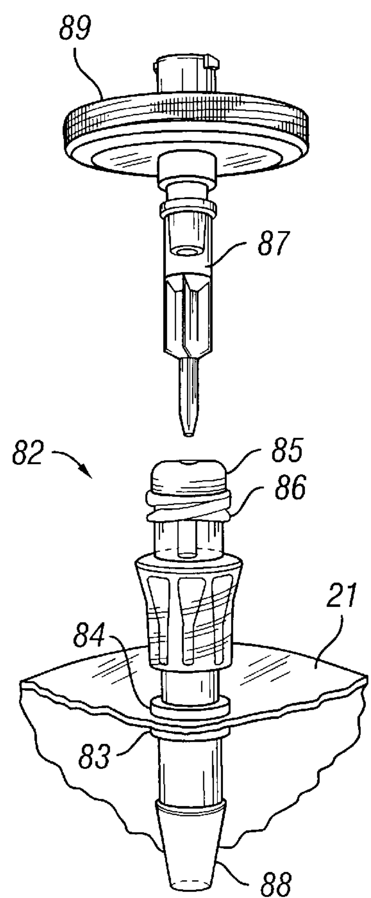
FIG. 10 shows a side view of one embodiment of a gas removal port.

To assist in filling the culture bag assembly 2, 20 or 500 with media, one or more gas removal means or fill means are incorporated into the bag assembly. As media is pumped into the bag, gas will be displaced and must have a release mechanism. There are a variety of means known in the art for releasing gas from media storage bags as the bags are filled with media. Similar gas releasing means will work in the present invention. A preferred embodiment of a gas releasing means is the gas removal port 82, shown in detail in FIG. 10. Preferably, the culture bag is totally filled with media and has zero headspace. The media is conditioned before it is pumped into the culture bag. Conditioned media has a particular pH and has been gassed to contain desired quantities of oxygen and/or other gases.

The gas removal port 82 transverses both sides of the bag 21 and is fused to the bag 21. Preferably an internal gasket 83 and an external gasket 84 are utilized to ensure that there is no leakage around the gas removal port 82 where it protrudes through the bag 21. The internal section 88 of the gas removal port 82 is open to the interior of the bag 21. The exterior section of the gas removal port 82 has a septum 85 and a luer lock coupler 86.

To release gas from the interior of the bag, the needle of a syringe may be inserted through the septum and the gas released through the syringe. However, a more efficient means, shown in FIG. 10, uses a fitting 87 having a sharp end to pierce the septum 85 and a coupling end to couple with an enclosed filter 89. Thus, when the fitting 87 is inserted through the septum 85, any gas in the interior of the bag can freely transverse the interior of the fitting 87 and pass through the filter 89. This gas releasing means allows large quantities of gas to be removed from the bag 21 while the bag is being filled with media. This gas releasing means also allows the bag 21 to be filled with media absent air bubbles that can cause unwanted turbulence. Furthermore, the filter (preferably having a 0.2 micron or less pore size) will prevent any contamination of the media in the event there is any back flow of air from the outside through the filter into the bag 21. In addition, once the fitting 87 has been removed, the septum 85 will reseal and provide an air-tight seal.

The bag 21 will also typically have an introduction means whereby media, cells, tissues, etc. can be introduced into the interior of the bag. There are numerous means known in the art by which the bag may be filled. In fact, the gas removal port 82, shown in FIG. 10 and described above, can be used to introduce small quantities of media or cells into the bag. Typically a syringe would be used to inject such materials into the bag through the septum 85. However, for rapidly filling the bag 21 or introducing certain tissue or organoid materials a larger port may be desired.

Figure 11:
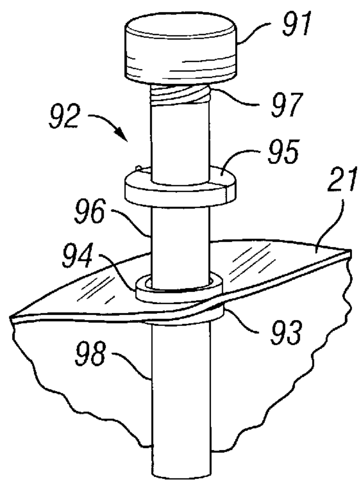
FIG. 11 shows a side view of one embodiment of a fill port.

One embodiment of a rapid fill port 92, illustrated in FIG. 11, transverses both sides of the bag 21 and is fused to the bag 21 in a similar manner as gas removal port 82. Preferably an internal gasket 93 and an external gasket 94 are utilized to ensure that there is no leakage around the rapid fill port 22 where it protrudes through the bag 21. The internal section 98 of the fill port 92 is open to the interior of the bag 21. The exterior section of the fill port 82 has a length of tubing 96 with a pinch clamp 95 to close off the end of the tubing 96 when the source of media is removed. Preferably there is an end coupler 97 that allows the end of the tubing 96 to be capped with a closed. For example, the end coupler 97 may be threaded or have a leur lock coupler for engaging a cap 91.

To assist in mixing the fluid in the bag assembly 2 or 20, one or more optional perfusion tubes will be incorporated into the bag assembly. Various types of perfusion tubes are used. For example, one or more attached outer perfusion tubes **22*a* are mounted on the interior of the bag wall. Each outer perfusion tube 22*a* is supported over its length, beginning a small distance from the inlet piece 25, by being joined integrally with a seam 24. The perfusion tube 22*a* is symmetrically positioned in the seam 24 and fused to the wall of bag 21 by welds 76 on each side of seam 24, as shown in FIGS. 16 and 17. The weld joints 76 only cover a portion of the circumference of the outer perfusion tubes 22*a*, so that a substantial portion of the tubes 22*a*** is still exposed to the interior volume of the bag.

Figure 12:
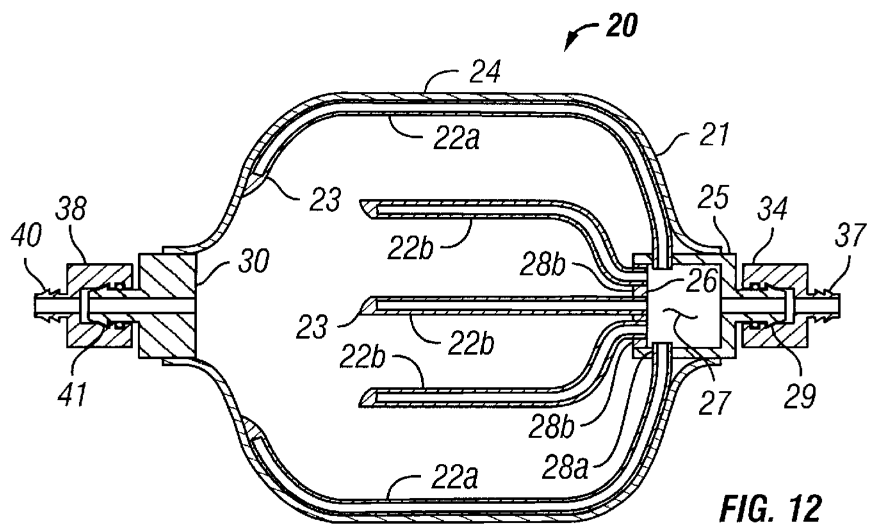
FIG. 12 is a longitudinal cross-section of another embodiment of the culture bag having internal perfusion tubes.
Figure 14:
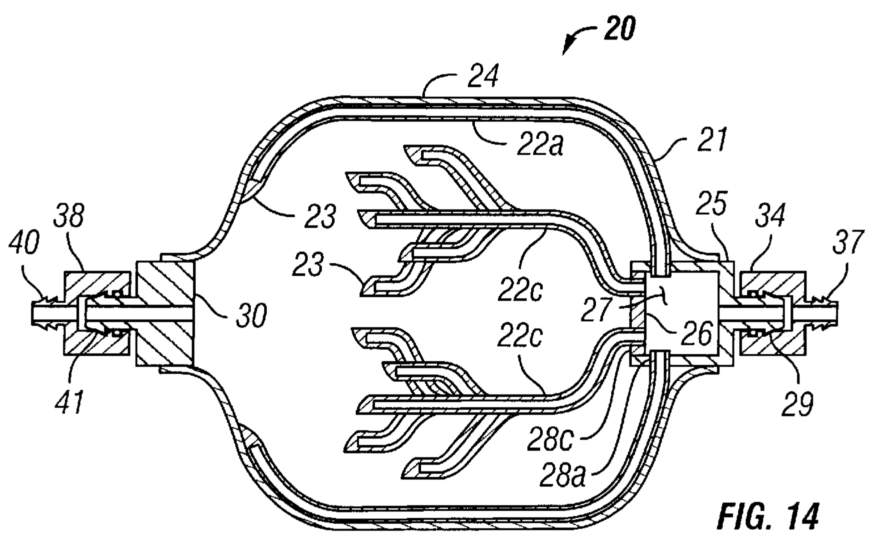
FIG. 14 is a longitudinal cross-section of another embodiment of the culture bag having branched internal perfusion tubes.

The bag 21 may also have one or more internal perfusion tubes of various configurations. For example, tubes **22*b* extend from the inlet end cap 26 into the interior of the bag 21 as shown in FIG. 12. Alternatively, the interior perfusion tubes 22*c* may be branched along its length. FIG. 14 illustrates one configuration of branched internal perfusion tubes 22*c*. Furthermore, some or all of the internal perfusion tubes 22*b,c* may be bonded to the seam 24 of the bag 21**.

The internal perfusion tubes **22*b* and 22*c* will vary in length, weight and flexibility, depending on the viscosity of the media. The internal perfusion tubes 22*b* and 22*c* move with the rotation of the bag support assembly 11, thus adding to the mixing of the media within the bag. Attachment of one or more distal ends of the internal perfusion tubes 22*b* or 22*c*** will limit the movement of the internal perfusion tubes within the interior of the culture bag during rotation of the culture bag.

Each perfusion tube **22*a,b,c* has a distal closure 23 where the perfusion tube is closed or sealed by crimping and/or fusing. In contrast, the proximal end of each perfusion tube 22*a,b,c* is in communication with the fluid inlet for the bag 21. The material of construction of perfusion tubes 22*a,b,c* is a biologically-compatible, nontoxic, non-protein-absorbing, flexible polymer having a number of perforations, allowing fresh media to be pumped into the bag 21** under a low pressure gradient, similar to a soaker hose used in watering lawns.

As shown in FIGS. 1–3, the exterior of the body of inlet end piece 25 is a right circular cylinder that is sized to have a slip fit within the central bore 17 of the bag support closure 13 or within the central bore 7 of the hinged bag support assembly 3. On the interior end of inlet end piece 25 is a counterbore that is closed by the closely fitting thin disk of inlet end cap 26. Inlet end cap 26 is fused to the counterbore of inlet end piece 25 at the outer end of the counterbore, thereby forming inlet header cavity or manifold 27. Radial branch ports **28*a* extend through the cylindrical wall of inlet end piece 25 and intersect inlet manifold 27. An attached outer perfusion tube 22*a* is fused into each branch port 28*a* so that the lumen of each tube 22*a* is in communication with inlet manifold 27**.

Whenever the bag 21 has interior perfusion tubes **22*b* or 22*c*, as shown in FIGS. 12–15, branch ports 28*b* and 28*c* are provided respectively in inlet end cap 26 coplanar with and at an angle to the axis of the inlet end cap. A cantilevered interior perfusion tube 22*b* or 22*c* is fused into each branch port 28*b* or 28*c* so that its lumen is in communication with inlet manifold 27. The construction of cantilevered interior perfusion tube 22*b* and 22*c* is similar to that of tube 22*a*, with the distal end of tube 22*b* and 22*c* closed by end closure 23**.

The exterior end of inlet end piece 25 has a transverse shoulder with a reduced diameter tubular inlet neck 29 extending outwardly concentric with the body of inlet end piece. Inlet neck 29 has a concentric flow passage connecting with inlet manifold 27. The outer end of the exterior of inlet neck 29 has a connection suitable for attaching the media inlet system (not shown). Such a connection may be a lead-in taper as shown in FIG. 1, or any other tip or connection end known in the art.

A first end of the sides of the bag 21, or the inlet mouth of the bag 21, is lapped onto and fused by weld 31 to the outer cylindrical surface of inlet end piece 25 to effect a seal therewith. Sufficient length of the outer end of the cylindrical body of inlet end piece 25 is uncovered by the fused lap joint with the bag 21 so that portion of the bag assembly can be supported within the coaxial center bore of the bag support closure 13.

Whenever the bag assembly 20 includes an inlet swivel 34, a rotational fluid coupling will be incorporated into the inlet swivel assembly. One example of such a fluid coupling is shown in FIG. 2. In this embodiment the exterior of inlet neck 29 has, from its outer end, a lead-in taper to permit engaging and seating without cutting an O-ring on the outer cylindrical surface of the inlet neck, a smooth cylindrical surface upon which an O-ring can seal, and a locking flange 30 constituting a conical ramp with a transverse face spaced apart from the transverse outer end of the cylindrical body of inlet end piece 25 by approximately 0.5 to 0.2 inch.

Inlet swivel joint 34 has a right circular cylindrical body with a rotational fluid coupling on its inner end and tubular inlet tubing connection 37 on its outer end. The outer surface of tubing connection 37 is constructed to permit engagement with a fluid supply connection. In this embodiment, tubing connection 37 is shown as a male strip-on tubing connector for use with flexible tubing. In the embodiment of the rotational fluid coupling shown in FIG. 2, the counterbored portion of the body of inlet swivel joint 34 has, in order from its interior end, a female O-ring groove containing O-ring 35 and a latching recess 36 consisting of a conical groove with a transverse outer shoulder. The latching recess is configured to comate with the locking flange 30 of inner end piece 25 so that inlet swivel joint 34 and inner end piece are connected and restrained against relative axial movement, but are able to rotate freely relative to each other. O-ring 35 seals with inlet neck 29 of inlet end piece 25. The axial hole in tubing connection 37 provides a flow passage from the fluid supply tubing of a bioreactor to the counterbore of inlet swivel joint 34. Other designs of a rotational fluid couplings may also be used.

The exterior of the body of outlet end piece 40 is a short right circular cylinder that provides a slip fit with the central bore 17 of first bag support end 12. The exterior end of outlet end piece 40 incorporates a rotational fluid coupling having a transverse shoulder with a reduced diameter outlet neck 41 extending outwardly concentric with the body of outlet end piece. Outlet neck 41 has a concentric flow passage that extends through the entire body of outlet end piece 40 to join with a rotational fluid coupling or swivel joint. The exterior of outlet neck has a tapered tip or other suitable connection for joining to the media outlet system.

Whenever the bag assembly 20 includes an outlet swivel joint, the exterior of outlet neck 41 has, from its outer end, a lead-in taper to permit engaging and seating without cutting an O-ring on the outer cylindrical surface of the outlet neck, a smooth cylindrical surface upon which an O-ring can seal, and a locking flange 42 constituting a conical ramp with a transverse face spaced apart from the transverse outer end of the cylindrical body of outlet end piece 40 by approximately 0.5 to about 0.2 inch. The other, outlet mouth of the bag 21 is lapped onto and fused by weld 44 to the outer cylindrical surface of outlet end piece 40 to effect a seal therewith. Sufficient length of the outer end of the cylindrical body of outlet end piece 40 is uncovered by the fused lap joint with the bag 21 so that portion of the bag assembly can be supported within the coaxial center bore of the bag support end 13. As shown here, the transverse outer face of outlet end piece 40 is provided with a unique patient identifier, such as a bar code 43, by which the bag and its contents can be traced through processing. As may be readily understood, the bar code may be placed at other suitable locations on bag assembly 20.

Outlet swivel joint 48 has a right circular cylindrical body with a rotational fluid connector on its inner end and an outlet tubing connection 52 on its outer end. In this embodiment the connector 52 is shown as a male flexible tubing connector. The embodiment of the rotational fluid connector illustrated in FIG. 2 includes a counterbored portion of the body of outlet swivel joint 48 having, in order from its interior end, a female O-ring groove containing O-ring 51 and a latching recess 49 consisting of a conical groove with a transverse outer shoulder. The latching recess is configured to comate with the locking flange 42 of outer end piece 40 so that outlet swivel joint 48 and outer end piece are connected and restrained against relative axial movement, but are able to rotate freely relative to each other. O-ring 51 seals with outlet neck 41 of outlet end piece 40. The axial hole in tubing connection neck 52 provides a flow passage to the fluid output tubing (not shown here) to the counterbore of outlet swivel joint 48. If necessary, the inlet or outlet rotational fluid coupling (e.g., the inlet swivel joint 34 and the outlet swivel joint 48) can be restrained against rotation by a variety of stop means such as restrained torque arms and the like. Typically, the torsional resistance of the fluid supply and output tubings is sufficient to avoid substantial rotation of the swivels.

Drive assembly 60 may have a variety of designs. In this embodiment the drive assembly 60 is similar to that used in U.S. Pat. No. 6,080,581, which is hereby incorporated by reference, where a rigid cylinder was used as the rotating bioreactor. The bag support assembly 11 that contains bag assembly 2, 20, or 500 is supported by two parallel, spaced-apart, journaled shaft assemblies, each mounting a set of one or more equidiameter rollers, such that the bag support assembly is tangential to both sets of rollers. At least one and, possibly, both shaft assemblies are driven. A driven shaft assembly 60 consists of variable speed motor 61 which has its output shaft connected to main shaft 63 by cylindrical shaft coupling 62. Shaft 63 is journaled in two places near its ends by bearings 65, which are in turn supported by pillow blocks 66. Equidiameter rollers 68 are concentrically mounted on main shaft 63 adjacent the pillow blocks 66 and positioned to support the bag support assembly 11 close to its ends. Motor 61 is mounted on base plate 69, as are the pillow blocks 66. If an undriven idler shaft assembly is used, then the shaft coupling 62 and motor 61 are omitted. If both shaft assemblies are driven, then they must be synchronized to run at the same speed. The motor driver or drivers are not indicated in FIGS. 1 or 2, and axial keeper rollers for maintaining bag support assembly 11 centered on the rollers of the shaft assemblies likewise are not shown. Both of these items and other minor items are well understood by those skilled in the art and are not essential for understanding the present invention.

Figure 18:
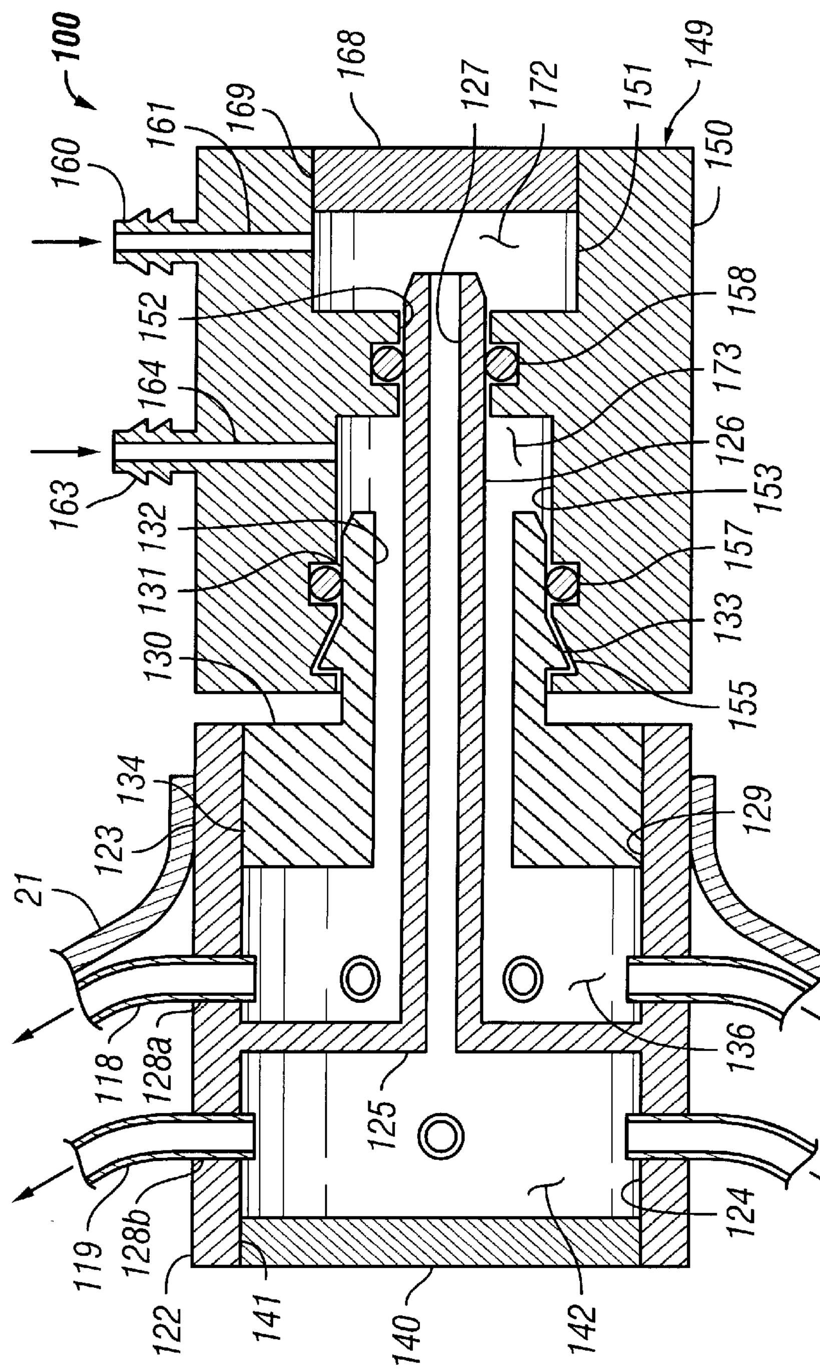
FIG. 18 shows a longitudinal cross-sectional view of an alternative embodiment of the inlet system of the culture bag, wherein a dual fluid coupling swivel joint is used to deliver two inlet fluid streams which are separately perfused into the culture bag.

FIG. 18 shows a different kind of bag inlet piece and inlet swivel joint which may be used to replace only those items of the bag assembly 20 of the embodiment shown in FIG. 2 of the rotating bag bioreactor system, thereby creating another embodiment 100 of the present invention. All other items of the previously described embodiment are the same for this embodiment, and so are not shown in FIG. 18. The inlet end piece 122 and the inlet swivel joint 149 are configured so that two separate input streams are kept separate and delivered separately to the biological media 14 by means of dedicated first 118 and second 119 attached perfusion tubes.

Referring to FIG. 18, the body of inlet end piece 122 consists of a right circular cylindrical segment with a bore

124 on its inner end. One mouth of the bag 21 is lapped onto and fused by weld 123 to the outer cylindrical surface of inlet end piece 122 to effect a seal therewith. Sufficient length of the outer end of the cylindrical body of inlet end piece 122 is uncovered by the fused lap joint with the bag 21 so that portion of the bag assembly can be supported within the coaxial center bore 7 or 17 of the bag support assembly 3 or 11 respectively. Outer end bore 129 extends slightly past midlength of the body of inlet end piece 122 to create fluid separation transverse partition 125 between inner end bore 124 and outer end bore 129.

A nozzle 126 for the second fluid extends coaxially from the outer side of transverse partition 125. Nozzle 126 has a coaxial flow passage 127, which extends through its entire length and through transverse partition 125. The exterior of nozzle 126 has a lead-in chamfer to permit engaging and seating without cutting an O-ring with the smooth outer cylindrical surface of the nozzle.

One or more radial branch ports 128*a* for the first fluid attached perfusion tubes 118 penetrate the cylindrical wall of the body of inlet end piece 122 adjacent the outer side of the transverse partition 125. One or more radial branch ports 128*b* for the second fluid attached perfusion tubes 119 penetrate the cylindrical wall of the body of inlet end piece 122 adjacent the inner side of the transverse partition 125. The first fluid perfusion tubes 118 are fused into the branch ports 128*a* and the second fluid perfusion tubes 119 are fused into branch ports 128*b*. Additional perfusion tubes may be fused with perfusion ports extending through interior traverse cap 140 in a manner analogous to that shown for perfusion tubes 22*b* and 22*c* as shown in FIGS. 12–15.

The exterior of the body of outer end cap 130 is a short right circular cylinder that is closely fitted to and sealingly fused to the outer bore of inlet end piece 122 by weld 134. The exterior end of outer end cap 130 has a transverse shoulder with a reduced diameter first fluid nozzle 131 extending outwardly concentric with the body of outer end cap. First fluid nozzle 131 has a concentric flow passage 132 that extends through the entire body of outer end cap 130. The diameter of flow passage 132 is sufficient to clear second fluid nozzle 126 with enough annular gap to provide an unrestricted flow path for the first fluid. The exterior of first fluid nozzle 131 has, from its outer end, a lead-in taper to permit engaging and seating without cutting an O-ring on the outer cylindrical surface of the outlet neck, a smooth cylindrical surface upon which an O-ring can seal, and a locking flange 133 constituting a conical ramp with a transverse face spaced apart from the transverse outer end of the cylindrical body of outer end cap 130 by approximately 0.5 to 0.2 inch. The annular region between the outer end bore 129, the second fluid nozzle 126, and the transverse partition 125, all of inlet end piece 122, and the transverse inner end of the body of outer end cap 130 serves as an inlet header 136 for the first fluid.

The first perfusion tubes 118 are thus connected to inlet header 136. Interior transverse cap 140 is a cylindrical disk which is closely fitted to and sealingly fused to inner end bore 124 of inlet end piece 122 by weld 141, thereby forming second fluid inlet header 142 between cap 140, partition 125, and bore 124. Second fluid header 142 is fed by flow passage 127 and in turn feeds second perfusion tubes 119.

The body 150 of inlet fluid coupling swivel joint assembly 149 is a right circular cylinder having a through bore 152 which has a close slip fit to the outer diameter of second fluid nozzle 126 of inlet end piece 122. Through bore 152 has a centrally located female O-ring groove containing O-ring 158 for effecting a seal with second fluid nozzle 126. Outer end counterbore 151 extends a short distance axially into body 150 and intersects through bore 152. Inner side counterbore 153 has, in order from its interior end, a female O-ring groove containing O-ring 157 and a latching recess 155 consisting of a conical groove with a transverse outer shoulder. The latching recess is configured to comate with the locking flange 133 of inlet end piece 122 so that inlet swivel joint 149 and the outer end cap 130 rigidly attached to inlet end piece 122 are connected and restrained against relative axial movement, but are able to rotate freely relative to each other. O-ring 157 seals with first fluid nozzle 131 of outer end cap 130.

Second fluid inlet tubing connection 160 and its concentric second fluid inlet flow passage 161 extend radially through the wall of body 150 and intersect outer counterbore 151 close to its inner end. First fluid inlet tubing connection 163 and its concentric first fluid inlet flow passage 164 extend radially through the wall of body 150 and intersect inner side counterbore 153 close to its inner end. The outer surface of inlet tubing connections 160 and 163 are ridged to permit engagement with the fluid input tubings (not shown) in a slip-on connection.

Outer transverse end cap 168 closely fits to and is sealingly fused to outer counterbore 151 by weld 169 to create second fluid inlet plenum 172 between cap 168 and outer counterbore 151. Second fluid inlet flow passage 161 is in communication with second fluid inlet plenum 172, flow passage 127 in second fluid nozzle 126, inlet header 142, and second fluid perfusion tubes 119.

Second fluid inlet plenum 173 is created between inner end counterbore 153, second fluid nozzle 126, and first fluid nozzle 131. First inlet flow passage 163 is in communication with first fluid inlet plenum 173, flow passage 132 in first fluid nozzle 131, inlet header 136, and first fluid perfusion tubes 118. O-ring 158 provides isolation of the first and second fluid streams from each other.

Figure 19:
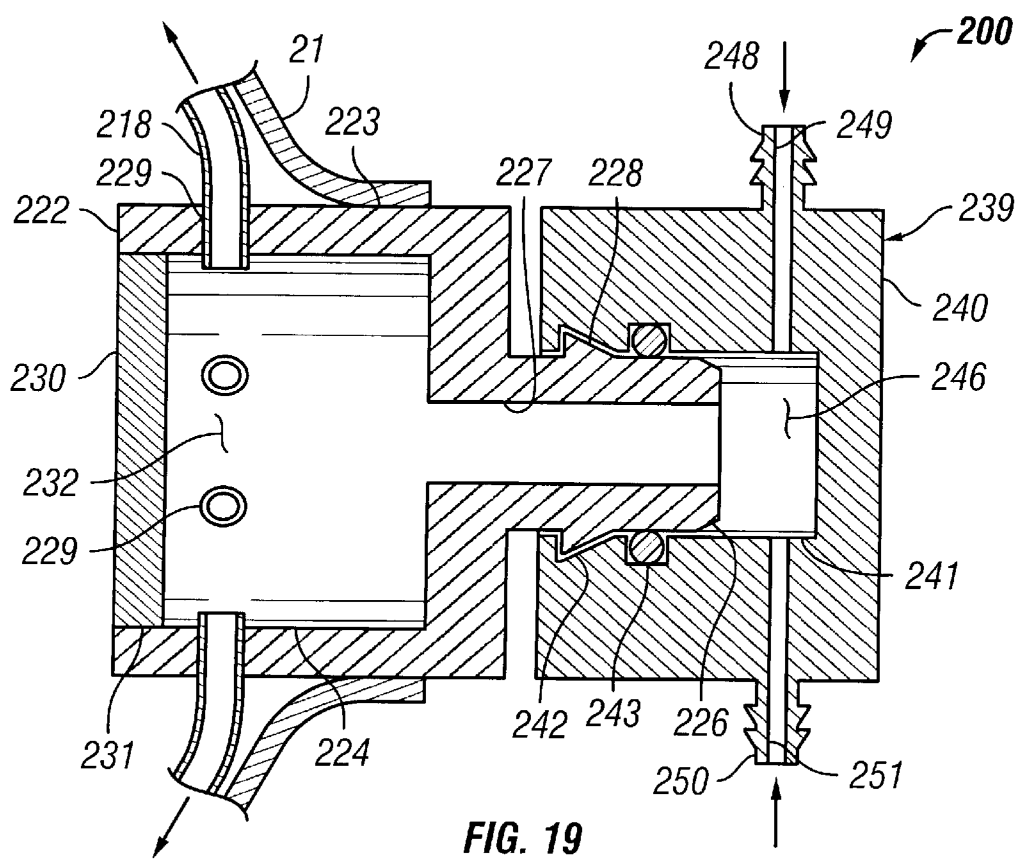
FIG. 19 shows a longitudinal cross-sectional view of another inlet system of the culture bag having dual fluid inputs through a fluid coupling swivel joint where the fluids are intermingled prior to perfusion into the culture bag.

FIG. 19 shows another bag inlet piece and inlet swivel joint which may be used to replace only those items of the bag assembly 20 of the embodiment shown in FIG. 2 of the rotating bag bioreactor system, thereby creating another embodiment 200 of the present invention. All other items of the previously described embodiment are the same for this embodiment, and so are not shown in FIG. 19. The inlet end piece 222 and the inlet fluid coupling swivel joint assembly 239 are configured so that the two initially separate input streams are commingled and delivered commingled together to the biological media 14 by means of attached perfusion tubes 218.

Referring to FIG. 19, the body of inlet end piece 222 consists of a right circular cylindrical segment with a counterbore 224 on its inner end. One mouth of the bag 21 is lapped onto and fused by weld 223 to the outer cylindrical surface of inlet end piece 222 to effect a seal therewith. Sufficient length of the outer end of the cylindrical body of inlet end piece 222 is uncovered by the fused lap joint with the bag 221 so that portion of the bag assembly can be supported within the coaxial center bore 7 or17 of the bag support assembly 3 or 11 respectively.

The exterior end of inlet end piece 222 has a cylindrical transverse shoulder with a reduced diameter fluid inlet nozzle 226 extending outwardly concentric with the body of inlet end piece. Fluid inlet nozzle 226 has a concentric flow passage 227 that extends through the entire body of inlet end piece 222 and communicates with counterbore 224. The exterior of fluid inlet nozzle 226 has, from its outer end, a lead-in taper to permit engaging and seating without cutting an O-ring on the outer cylindrical surface of the outlet neck, a smooth cylindrical surface upon which an O-ring can seal, and a locking flange 228 constituting a conical ramp with a transverse face spaced apart from the transverse outer end of the cylindrical body of inlet end piece 222 by approximately 0.5 to 0.2 inch. Counterbore 224 on the interior end of inlet end piece 222 is closed by the closely fitting thin disk of inner end transverse cap 230, which is sealingly fused by weld 231 to the counterbore of inlet end piece 222 at the outer end of the counterbore, thereby forming plenum chamber 232.

One or more radial branch ports 229 extend through the cylindrical wall of inlet end piece 222 and intersect inlet plenum chamber 232. An attached perfusion tube 218 is fused into each branch port 229 so that the lumen of each tube 218 is in communication with inlet plenum chamber 232. The construction of cantilevered perfusion tube 218 is identical to that of tube 22*a* shown in FIG. 1, wherein the distal end of tube 22*b* is closed by end closure 23. Additional perfusion tubes may be fused with perfusion ports extending through inner end traverse cap 230 in a manner analogous to that shown for perfusion tubes 22*b* and 22*c* shown in FIGS. 12–15.

The body 240 of inlet swivel joint 239 is a right circular cylinder with a bore 241 on its inner end. The bore 241 of the body 240 of inlet swivel joint 239 has, in order from its interior end, a female O-ring groove containing O-ring 243 and a latching recess 242 consisting of a conical groove with a transverse outer shoulder. The latching recess is configured to comate with the locking flange 228 of inner end piece 222 so that inlet swivel joint 239 and inner end piece are connected and restrained against relative axial movement, but are able to rotate freely relative to each other. O-ring 243 seals with fluid inlet nozzle 226 of inlet end piece 222. Entry plenum 246 is formed between bore 241 and fluid inlet nozzle 226.

Radially positioned first fluid inlet tubing connection 248 has concentric first fluid inlet flow passage 249 that penetrates the wall of body 240 to communicate with entry plenum 246. Radially positioned second fluid inlet tubing connection 250 has concentric second fluid inlet flow passage 251 that penetrates the wall of body 240 to communicate with entry plenum 246. As shown, the fluid inlet tubing connections 248 and 250 are diametrically opposed. The outer surface of fluid inlet tubing connections 248 and 250 are ridged to permit sealing engagement with fluid input tubings (not shown) in slip-on connections.

The axial flow passage 227 in fluid inlet nozzle 226 provides a flow passage to the plenum chamber 232 of the inlet end piece from the entry plenum 246 and hence to the inlet perfusion tubes 218. If necessary, the inlet swivel joint 239 can be restrained against rotation by a variety of stop means such as restrained torque arms and the like. Typically, the torsional resistance of the fluid supply tubings is sufficient to avoid substantial rotation of the swivel.

Figure 20:
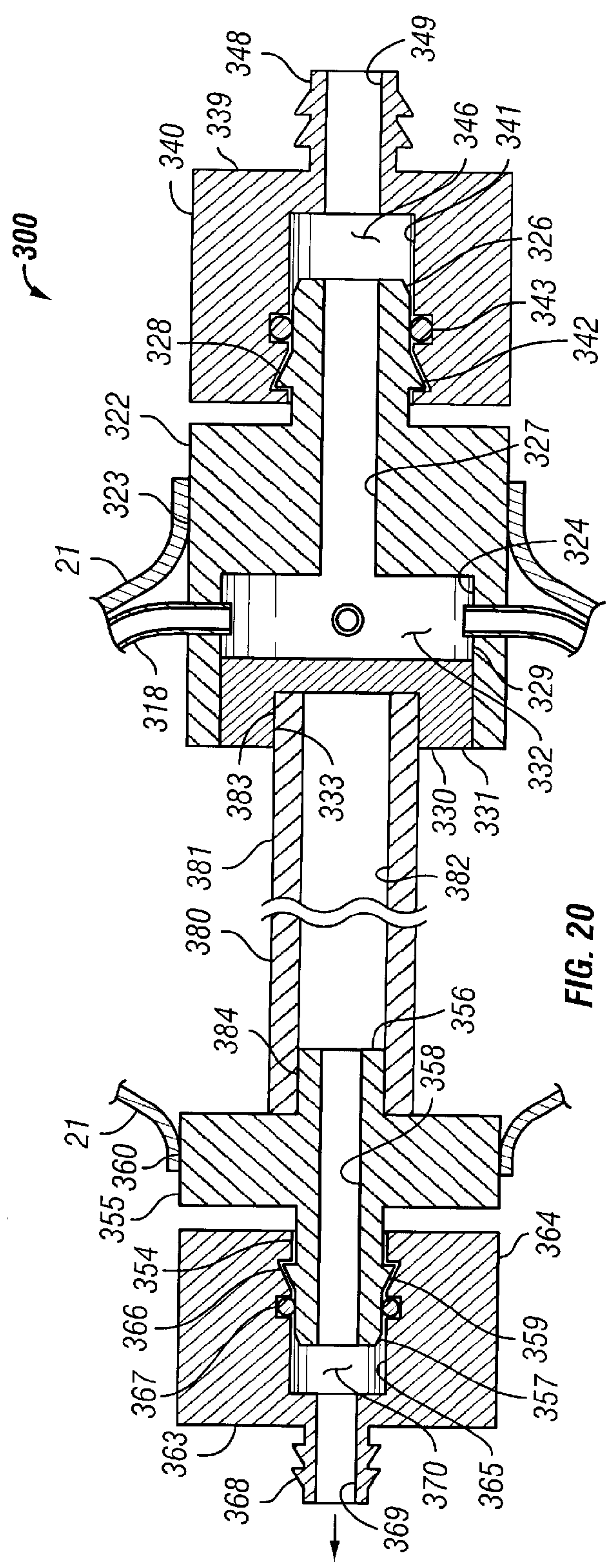
FIG. 20 shows a partial longitudinal cross-sectional view of an alternative embodiment of the culture bag having an axially positioned outlet filter extending the interior length of the bag.

FIG. 20 shows yet another kind of bag inlet piece and outlet piece with an integral axially positioned internal filter element which may be used to replace only those items of the bag assembly 20 of the rotating bag bioreactor system shown in FIG. 2, thereby creating yet another embodiment 300 of the present invention. All other items of the first described embodiment are the same for this embodiment, and so are not shown in FIG. 20. Although this embodiment of the inlet and outlet piece for the bag assembly 20 is illustrated in FIG. 20, this embodiment of the inlet and outlet piece can also be used with bag assemblies 2 and 500.

The inlet end piece 322 and the outlet end piece are configured so that the two jointly support in an axial position a tubular filter element 380 in the biological media 14. The tubular filter element is a selectively permeable element and designed to allow biological products being produced in the bioreactor to be readily removed with the spent media from the interior of the bag, while retaining cells, cellular aggregates, particles, tissues and organoids within the bag. For example, a therapeutic protein produced by a genetically engineered cell would pass through the filter and be removed from the culture bag as fresh media is pumped into the culture bag and spent media is withdrawn from the bag, whereas the cells would not pass through the filter and would remain inside of the culture bag. In a preferred embodiment, the culture bag is rotated along the longitudinal axis of the bag support assembly and the cells, cellular aggregates, particles, tissues and organoids are continually suspended while the media is allowed to pass through the tubular filter. Preventing the cells, cellular aggregates, particles, tissues and organoids from settling on the filter while filtering the media increases the efficiency of the filtration.

Referring to FIG. 20, the body of inlet end piece 322 consists of a right circular cylindrical segment with a counterbore 324 on its inner end. The exterior of the body of inlet end piece 322 is a short right circular cylinder that provides a slip fit with the central bore of the bag support assembly 3 or 11. One mouth of the bag 21 is lapped onto and fused by weld 323 to the outer cylindrical surface of inlet end piece 322 to effect a seal therewith. Sufficient length of the outer end of the cylindrical body of inlet end piece 322 is uncovered by the fused lap joint with the bag 21 so that portion of the bag assembly can be supported within the coaxial center bore 7 or 17 of the bag support assembly 3 or 11 respectively.

The exterior end of inlet end piece 322 has a cylindrical transverse shoulder with a reduced diameter fluid inlet nozzle 326 extending outwardly concentric with the body of inlet end piece. Fluid inlet nozzle 326 has a concentric flow passage 327 that extends through the entire body of inlet end piece 322 and communicates with counterbore 324. The exterior of fluid inlet nozzle 326 has, from its outer end, a lead-in taper to permit engaging and seating without cutting an O-ring on the outer cylindrical surface of the outlet neck, a smooth cylindrical surface upon which an O-ring can seal, and a locking flange 328 constituting a conical ramp with a transverse face spaced apart from the transverse outer end of the cylindrical body of inlet end piece 322 by approximately 0.5 to 0.2 inch.

Counterbore 324 on the interior end of inlet end piece 322 is closed by the closely fitting thick disk of inner end transverse cap 330, which is sealingly fused by weld 331 to the counterbore of inlet end piece 322 at the outer end of the counterbore, thereby forming plenum chamber 332. Inner end transverse cap 330 has a flat-bottomed shallow blind bore 333 on its interior face. This blind bore 333 is sized to closely fit the outer diameter of axial filter element 380. One or more radial branch ports 329 extend through the cylindrical wall of inlet end piece 322 and intersect inlet plenum chamber 332. An attached perfusion tube 318 is fused into each branch port 329 so that the lumen of each tube 318 is in communication with inlet plenum chamber 332. The construction of cantilevered perfusion tube 318 is identical to that of tube 22*a* shown in FIG. 1, wherein the distal end of tube 22*a* is closed by end closure 23. Additional perfusion tubes may be fused with perfusion ports extending through interior traverse cap 330, on either side of the filter element 380, in a manner analogous to that shown for perfusion tubes 22*b* and 22*c* as shown in FIGS. 12–15.

Inlet fluid coupling swivel joint assembly 339 has a right circular cylindrical body 340 with a counterbore 341 on its inner end and an inlet tubing connection 348 on its outer end. The counterbore 341 of the body 340 of inlet fluid coupling swivel joint assembly 339 has, in order from its interior end, a female O-ring groove containing O-ring 343 and a latching recess 342 consisting of a conical groove with a transverse outer shoulder. The latching recess is configured to comate with the locking flange 328 of inner end piece 322 so that inlet swivel joint 339 and inner end piece 322 are connected and restrained against relative axial movement, but are able to rotate freely relative to each other. O-ring 343 seals with fluid inlet nozzle 326 of inlet end piece 322.

Entry plenum 346 is formed between bore 341 and fluid inlet nozzle 326. The axial through hole inlet flow passage 349 in inlet tubing connection 348 provides a flow passage for the fluid input tubing (not shown here) to the entry plenum 346 of inlet swivel joint assembly 339. The axial flow passage 327 in fluid inlet nozzle 326 provides a flow passage to the plenum chamber 332 of the inlet end piece 322 from the entry plenum 346 and hence to the inlet perfusion tubes 318. The outer surface of fluid inlet tubing connection 348 is ridged to permit sealing engagement with the fluid input tubing (not shown) by means of a slip-on connection.

The exterior of the central cylindrical flange body 355 of outlet end piece 354 is a right circular cylinder which provides a slip fit with the central bore of bag support assembly 3 or 11. The interior end of body 355 is a concentric cylindrical inner boss 356 that has a reduced diameter relative to the body 355. The outer diameter of boss 356 is a close fit to the inner diameter of axial filter 380. The exterior end of outlet end piece 354 has a transverse shoulder with a reduced diameter fluid outlet nozzle 357 extending outwardly concentric with the body 355 of outlet end piece 354. Fluid outlet nozzle 357 has a concentric outlet flow passage 358 that extends through the entire body of outlet end piece 354. The exterior of fluid outlet nozzle 357 has, from its outer end, a lead-in chamfer to permit engaging and seating without cutting an O-ring on the outer cylindrical surface of the fluid outlet nozzle, a smooth cylindrical surface upon which an O-ring can seal, and a locking flange 359 constituting a conical ramp with a transverse face spaced apart from the transverse outer end of the cylindrical body 355 of outlet end piece 354 by approximately 0.5 to 0.2 inch. The other, outlet mouth of the bag 21 is lapped onto and fused by weld 360 to the outer cylindrical surface of the body of outlet end piece 354 to effect a seal therewith. Sufficient length of the outer end of the cylindrical body 355 of outlet end piece 354 is uncovered by the fused lap joint with the bag 21 so that portion of the overall bag assembly can be supported within the coaxial center bore of the bag support assembly.

Outlet fluid coupling swivel joint assembly 363 has a right circular cylindrical body 364 with a concentric counterbore 365 on its inner end and a concentric fluid outlet tubing connection 368 on its outer end. The counterbore 365 of the body 364 of outlet swivel joint assembly 363 has, in order from its interior end, a female O-ring groove containing O-ring 367 and a latching recess 366 consisting of a conical groove with a transverse outer shoulder. The latching recess is configured to comate with the locking flange 359 of outlet end piece 354 so that outlet swivel joint assembly 363 and outlet end piece 354 are connected and restrained against relative axial movement, but are able to rotate freely relative to each other. O-ring 367 seals with fluid outlet nozzle 357 of outlet end piece 354.

Outlet plenum 370 is formed between counterbore 365 and fluid outlet nozzle 357. The axial through hole outlet flow passage 369 in outlet tubing connection 368 provides a flow passage for the fluid output tubing (not shown here) from the outlet plenum 370 of outlet swivel joint assembly 363. The axial flow passage 358 in fluid outlet nozzle 357 provides a flow passage to the outlet plenum chamber 370 from the interior end entry of flow passage 358 (surrounded by the filter 380) and hence to the output flow. The outer surface of fluid outlet tubing connection 368 is ridged to permit sealing engagement with the fluid output tubing (not shown) by means of a slip-on connection. If necessary for either or both the inlet swivel joint assembly 339 and the outlet swivel joint assembly 363, the swivel joints can be restrained against rotation by a variety of stop means such as restrained torque arms and the like. Typically, the torsional resistance of the fluid supply and output tubings is sufficient to avoid substantial rotation of the swivels.

Axial filter 380 is constructed of biologically compatible material with a predetermined permeability to selected constituents of the biological media 14 within bag 21. Filter 380 is a right circular cylindrical tube having filter outer surface 381 and filter inner surface 382. The first end of filter 380 is inserted into the blind bore 333 of inner end transverse cap 330 or inlet end piece 322, where its outer surface 381 is sealingly fused together with cap 330 by weld 383. The second end of filter 380 is slipped over inner boss 356 of outlet end piece 354 where its inner surface 382 is sealingly fused to the cylindrical surface of boss 356 by weld 384. The inner lumen of filter 380 is thus isolated from the interior of bag 21 and in communication with the outlet passage of outlet end piece 354 and outlet swivel joint assembly 363. The axial filter 380 is typically designed to allow the permeability of proteins and/or cell metabolites without allowing the cells or tissues within the culture bag to pass into the inner lumen of filter 380.

Figure 21:
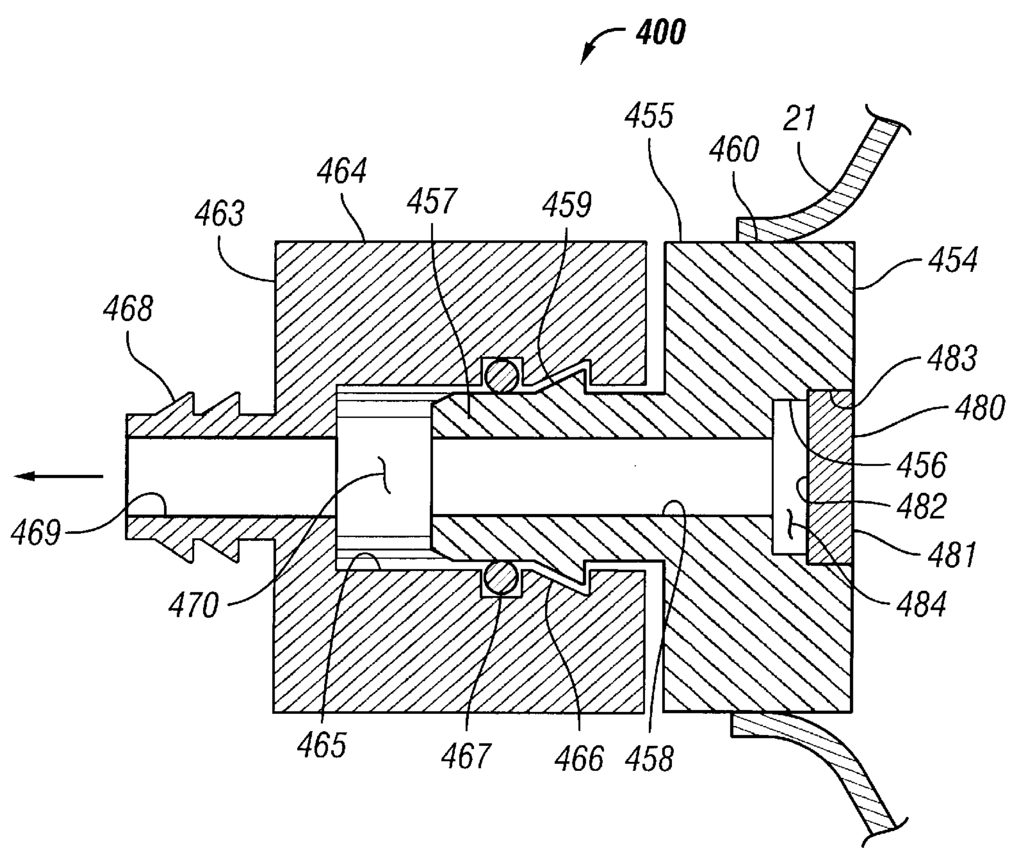
FIG. 21 is a partial longitudinal cross-sectional view of one embodiment of the outlet system, wherein an outlet filter is positioned at the upstream end of the outlet end piece flow channel.

FIG. 21 shows a bag outlet piece with an integral axially positioned outlet disk filter. A similar filter may also be incorporated into the inlet means. The exterior of the cylindrical body 455 of outlet end piece 454 is a right circular cylinder that provides a slip fit with the central bore of bag support end 12. The interior end of body 455 has a stepped concentric counterbore 456 that has a slightly larger diameter for the outer section of the counterbore. The larger outer diameter of counterbore 456 is a close fit to the outer diameter of disk filter 480. The exterior end of outlet end piece 454 has a transverse shoulder with a reduced diameter fluid outlet nozzle 457 extending outwardly concentric with the body 455 of outlet end piece 454. Fluid outlet nozzle 457 has a concentric outlet flow passage 458 that extends through the entire body of outlet end piece 454. The exterior of fluid outlet nozzle 457 has, from its outer end, a lead-in chamfer to permit engaging and seating without cutting an O-ring on the outer cylindrical surface of the fluid outlet nozzle, a smooth cylindrical surface upon which an O-ring can seal, and a locking flange 459 constituting a conical ramp with a transverse face spaced apart from the transverse outer end of the cylindrical body 455 of outlet end piece 454 by approximately 0.5 to 0.2 inch. The other, outlet mouth of the bag 21 is lapped onto and fused by weld 460 to the outer cylindrical surface of the body of outlet end piece 454 to effect a seal therewith. Sufficient length of the outer end of the cylindrical body 455 of outlet end piece 454 is uncovered by the fused lap joint with the bag 21 so that portion of the overall bag assembly can be supported within the coaxial center bore of the bag support end 12.

Outlet swivel joint assembly 463 has a right circular cylindrical body 464 with a concentric counterbore 465 on its inner end and a concentric fluid outlet tubing connection 468 on its outer end. The counterbore 465 of the body 464 of outlet swivel joint assembly 463 has, in order from its interior end, a female O-ring groove containing O-ring 467 and a latching recess 466 consisting of a conical groove with a transverse outer shoulder. The latching recess is configured to comate with the locking flange 459 of outlet end piece 454 so that outlet swivel joint assembly 463 and outlet end piece 454 are connected and restrained against relative axial movement, but are able to rotate freely relative to each other. O-ring 467 seals with fluid outlet nozzle 457 of outlet end piece 454. Outlet plenum 470 is formed between counterbore 465 and fluid outlet nozzle 457. The axial through hole outlet flow passage 469 in outlet tubing connection 468 provides a flow passage for the fluid output tubing (not shown here) from the outlet plenum 470 of outlet swivel joint assembly 463. The axial flow passage 458 in fluid outlet nozzle 457 provides a flow passage to the outlet plenum chamber 470 from the interior end entry of flow passage 458 at its intersection with the smaller of the stepped counterbores 456 (isolated by the filter disk 480) and hence to the output flow. The outer surface of fluid outlet tubing connection 468 is ridged to permit sealing engagement with the fluid output tubing (not shown) by means of a slip-on connection. If necessary for either or both the outlet end piece 454 or the outlet swivel joint assembly 463, the swivel joints can be restrained against rotation by a variety of stop means such as restrained torque arms and the like. Typically, the torsional resistance of the fluid supply and output tubings is sufficient to avoid substantial rotation of the swivels.

Axial filter 480 is constructed of biologically compatible material with a predetermined permeability to selected constituents of the biological media 14 within bag 21. Filter 480 is a right circular cylindrical disk that closely fits within the larger of the counterbores 456 of outlet end piece 454 and shoulders against the step between the counterbores. The cylindrical surface of filter 480 is sealingly fused to the larger of the counterbores 456 by weld 483. The filter outer surface 481 is thus exposed to the biological media 14 within the bag 21, while the inner filter surface serves with the smaller of the counterbores 356 to create collection plenum 484 to collect filtered fluid from the bag and supply it to the outlet flow path of the assembly 400.

The general use of the different bag assemblies described herein is similar. Basically, the bag support assembly 3 or 11 is opened and a prepared bag assembly 2, 20 or 500 is inserted into the bag support assembly so that the exposed cylindrical surface of the body of outlet end piece 40 is mounted in and supported by the central hole in the transverse end bulkhead of bag support assembly 3 or 11. The bag support assembly is closed and may be placed on the rollers 68 of drive assembly 60.

Although the present invention and its advantages have been described in detail, it should be understood that various changes, substitutions and alterations can be made herein without departing from the spirit and scope of the invention as defined by the appended claims.

What is claimed is:

1. A culture bag comprising:

at least one sheet having a first end, a second end, an internal side, and an external side, wherein the internal side of said sheet is positioned to face an interior of the culture bag;

a seam formed by fusing overlapped sections of one or more sheets;

an inlet means fused to the first end of one or more sheet;

an outlet means fused to the second end of one or more sheet; and at least one outer perfusion tube, wherein a proximal end of the outer perfusion tube is in fluid communication with the inlet means, a central section of an external surface of the outer perfusion tube is fused to an interior-surface of the seam, and a distal end of the outer perfusion tube is closed.

2. The culture bag of claim 1, wherein the sheet is made of a biocompatible material.

3. The culture bag of claim 1, wherein the sheet is made of a substantially gas impermeable material.

4. The culture bag of claim 1, wherein the sheet is made of a gas permeable material.

5. The culture bag of claim 1, wherein the sheet is made of a multilayered material.

6. The culture bag of claim 1, wherein the sheet is made of a flexible material.

7. The culture bag of claim 1, wherein said inlet means comprises an inlet end piece and an inlet fluid coupling swivel joint.

8. The culture bag of claim 1, wherein said inlet end piece includes an inlet manifold and a branch port.

9. The culture bag of claim 8, wherein an external surface of the proximal end of the outer perfusion tube is fused to the branch port and a lumen of the outer perfusion tube is in fluid communication with the inlet manifold and the interior of the culture bag.

10. The culture bag of claim 1, wherein said inlet means comprises:

an inlet fluid coupling swivel joint;

an inlet manifold;

a branch port, wherein an external surface of the proximal end of the outer perfusion tube is fused to the branch port and a lumen of the outer perfusion tube is in fluid communication with the inlet manifold and the interior of the culture bag; and a plurality of inlets, said inlets in fluid communication with the inlet manifold and the lumen of the outer perfusion tube.

11. The culture bag of claim 1, wherein said inlet means includes a plurality of inlets, each inlet introducing an independent fluid stream into the culture bag.

12. The culture bag of claim 1, wherein said outlet means comprises an outlet end piece and an outlet fluid coupling swivel joint.

13. The culture bag of claim 1, wherein said outlet means includes an outlet filter.

14. The culture bag of claim 13, wherein said outlet filter has a predetermined porosity.

15. The culture bag of claim 1, wherein the inlet means and the outlet means are coaxial.

16. The culture bag of claim 1, wherein the inlet means and the outlet means are configured to fit within concentric apertures on opposed ends of a rotating bioreactor chamber.

17. The culture bag of claim 1, further comprising an internal perfusion tube extending from an interior side of the inlet means into the interior of the culture bag.

18. The culture bag of claim 1, further comprising a plurality of internal perfusion tubes extending from an interior side of the inlet means into the interior of the culture bag.

19. The culture bag of claim 1, further comprising a plurality of internal perfusion tubes extending from an interior side of the inlet means into the interior of the culture bag, wherein the internal perfusion tubes have different lengths.

20. The culture bag of claim 1, further comprising a plurality of internal perfusion tubes extending from an interior side of the inlet means into the interior of the culture bag, wherein at least one internal perfusion tube has a distal end attached to the seam.

21. The culture bag of claim 1, further comprising an internal perfusion tube extending from an interior side of the inlet means into the interior of the culture bag, wherein the internal perfusion tube is branched.

22. The culture bag of claim 1, further comprising a plurality of internal perfusion tubes extending from an interior side of the inlet means into the interior of the culture bag, wherein the internal perfusion tubes are branched and at least one branch of at least one internal perfusion tube is attached to the seam.

23. The culture bag of claim 1, further comprising an internal perfusion tube extending from an interior side of the inlet means into the interior of the culture bag, wherein the internal perfusion tube has multiple perforations.

24. The culture bag of claim 1, further comprising an internal perfusion tube extending from an interior side of the inlet means into the interior of the culture bag, wherein the internal perfusion tube is designed to float in a media having a predetermined specific gravity.

25. The culture bag of claim 1, further comprising a gas removal means.

26. The culture bag of claim 1, further comprising a fill port.

27. The culture bag of claim 1, further comprising a gas removal means and a fill port.

28. The culture bag of claim 1, further comprising a patient identifier.

29. The culture bag of claim 28, wherein the patient identifier is a bar code.

30. The culture bag of claim 1, further comprising an internal tubular filter element extending from an interior end of the inlet means to the outlet means, wherein a lumen of said filter element is in fluid communication with said outlet means.

31. A culture bag comprising:

a plurality of sheets having a first end, a second end, an internal side, an external side and two opposed edges, wherein one edge of each sheet is fused with one edge of an adjacent sheet to form a seam, and wherein the internal sides of said fused sheets are positioned within an interior of the bag;

an inlet means fused to the first end of at least one sheet, wherein the inlet means includes an inlet end piece and an inlet fluid coupling swivel joint; and an outlet means fused to the second end of at least one sheet, wherein the outlet means comprises an outlet end pierce and an outlet fluid coupling swivel joint.

32. The culture bag of claim 31, said inlet means further comprising an inlet manifold and a plurality of inlets, said inlets in communication with the inlet manifold and the interior of the culture bag.

33. The culture bag of claim 31, wherein said outlet means includes an outlet filter.

34. The culture bag of claim 31, further comprising an internal tubular filter element extending from an interior end of the inlet means to the outlet means, wherein a lumen of said filter element is in fluid communication with said outlet means.

35. The culture bag of claim 31, further comprising a gas removal means.

36. The culture bag of claim 31, further comprising a fill port.

37. The culture bag of claim 31, further comprising a patient identifier.

38. The culture bag of claim 31, further comprising an outer perfusion tube, wherein a proximal end of the perfusion tube is in fluid communication with the inlet means, a section of an external surface of the perfusion tube is fused to an interior surface of one seam, and a distal end of the perfusion tube is closed.

39. The culture bag of claim 31, wherein the inlet means further comprises a manifold and a plurality of branch ports.

40. The culture bag of claim 39, further comprising a plurality of perfusion tubes extending from the inlet means into the interior of the culture bag, said perfusion tubes in fluid communication with the manifold and the interior of the culture bag.

41. The culture bag of claim 40, wherein the inlet means further comprises a plurality of inlets, each inlet introducing an independent fluid stream into the interior of the culture bag.

42. The culture bag of claim 41, wherein each inlet is in communication with at least one perfusion tube.

43. A culture bag comprising:

at least one sheet having a first end, a second end, an internal side, and an external side, wherein the internal side of said sheet is positioned to face an interior of the culture bag;

a seam formed by fusing overlapped sections of one or more sheets;

an inlet means fused to the first end of one or more sheet;

an outlet means fused to the second end of one or more sheet; and at least one outer perfusion tube having a proximal end, a central section and a distal end, wherein the proximal end is in fluid communication with the inlet means, a portion of an external surface of the central section is fused to an interior surface of the seam, and the distal end is closed, and further wherein the central section of the outer perfusion tube is perforated to allow fluid communication between a lumen of the outer perfusion tube and the interior of the culture bag; and at least one perforated internal perfusion tube, said internal perfusion tube in fluid communication with the inlet means and the interior of the culture bag.

44. The culture bag of claim 43, wherein the inlet means comprises:

an inlet fluid coupling swivel joint;

an inlet manifold;

a plurality of branch ports extending from the inlet manifold, wherein the proximal end of one outer or internal perfusion tube is fused to a side of each branch port; and a plurality of inlets, wherein each inlet introduces an independent fluid stream into one outer or internal perfusion tube.

45. The culture bag of claim 43, wherein the inlet means comprises:

an inlet fluid coupling swivel joint;

an inlet manifold;

a plurality of branch ports extending from the inlet manifold, wherein the proximal end of one outer or internal perfusion tube is fused to a side of each branch port; and a plurality of inlets, said inlets in fluid communication with the inlet manifold and the lumen of the outer or internal perfusion tubes.

46. The culture bag of claim 43, wherein said inlet means comprises an inlet end piece and an inlet fluid coupling swivel joint.

47. The culture bag of claim 43, wherein said outlet means comprises an outlet end piece and an outlet fluid coupling swivel joint.

48. The culture bag of claim 43, further comprising a patient identification means.

49. The culture bag of claim 43, further comprising an internal filter element, the filter element extends from an interior end of the inlet means to the outlet means, wherein a lumen of the filter element is in fluid communication with the outlet means.

50. A culture bag of claim 43, further comprising inlet tubing and outlet tubing.

51. A culture bag comprising:

at least one sheet having a first end, a second end, an internal side, and an external side, wherein the internal side of said sheet is positioned to face an interior of the culture bag;

a seam formed by fusing overlapped sections of one or more sheets;

an inlet means fused to the first end of one or more sheet, wherein the inlet means includes an inlet end piece, an inlet fluid coupling swivel joint, a manifold and a branch port;

an outlet means fused to the second end of one or more sheet, wherein the outlet means includes an outlet end piece and an outlet fluid coupling swivel joint; and a perforated perfusion tube, an external surface of a proximal end of the perfusion tube fused to the branch port and a lumen of the perfusion tube in communication with the manifold and the interior of the culture bag.

* * * * *